US009187523B2

(12) United States Patent
Motin et al.

(10) Patent No.: US 9,187,523 B2

(45) Date of Patent: Nov. 17, 2015

(54) SUBSTRATE PEPTIDE SEQUENCES FOR PLAGUE PLASMINOGEN ACTIVATOR AND USES THEREOF

(75) Inventors: Vladimir L. Motin, League City, TX (US); Sadhana Chauhan, League City, TX (US); Scott R. Gilbertson, Galyeston, TX (US); Anton Agarkov, Galyeston, TX (US); Pedro Lory, Antwerp (BE)

(73) Assignee: The Board of Regents of the University of Texas System, Austin, TX (US)

( * ) Notice: Subject to any disclaimer, the term of this patent is extended or adjusted under 35 U.S.C. 154(b) by 1047 days.

(21) Appl. No.: 13/199,407

(22) Filed: Aug. 29, 2011

(65) Prior Publication Data

US 2012/0045474 A1 Feb. 23, 2012

Related U.S. Application Data

(62) Division of application No. 11/901,978, filed on Sep. 20, 2007, now Pat. No. 8,030,447.

(60) Provisional application No. 60/845,850, filed on Sep. 20, 2006.

(51) Int. Cl.

| | |
|---|---|
| ***C12Q 1/37*** | (2006.01) |
| ***C12Q 1/02*** | (2006.01) |
| ***C07K 5/11*** | (2006.01) |
| ***C07K 5/072*** | (2006.01) |
| ***C07K 5/09*** | (2006.01) |
| ***C07K 7/06*** | (2006.01) |
| *A61K 38/00* | (2006.01) |

(52) U.S. Cl.

CPC ........... *C07K 5/1019* (2013.01); *C07K 5/06095* (2013.01); *C07K 5/0817* (2013.01); *C07K 7/06* (2013.01); *C12Q 1/37* (2013.01); *A61K 38/00* (2013.01)

(58) Field of Classification Search

CPC .................................. C12Q 1/37; C12Q 1/02

USPC .......................................................... 435/24

See application file for complete search history.

(56) References Cited

U.S. PATENT DOCUMENTS

| | | | |
|---|---|---|---|
| 5,602,021 | A | 2/1997 | Davis et al. |
| 7,335,504 | B2 | 2/2008 | Haupts et al. |
| 7,344,856 | B1 | 3/2008 | Okuno et al. |

OTHER PUBLICATIONS

Agarkov et al., Biopolymers, 2006, 84, 48-73.
Anderson G. et al., Infect Immun, 1996, 64, 4580-4585.
Baker et al., J Org Chem, 2000, 65, 9065-9058.
Bartlet et al., J Org Chem, 1995, 60, 3107-3111.
Beesley E. et al., J Bacteriol, 1967, 94, 19-26.
Benner G.E. et al., Infect Immun, 1999, 67, 1922-1928.
Billich et al., Biochem Pept Antibiot, 1990, 57-79.
Dai et al., Biorg Med Chem Lett, 2003, 13, 3817-3820.
Dive et al., Intern'l Journal of Peptide & Protein Research, 1992, 39, 506-515.
Easterbrook T. et al., Cont Microb Immunol, 1995, 13, 214-215.
Feichtinger et al., J Org Chem, 1998, 63, 3804-3805.
Fischer, Current Protein and Peptide Science, 2003, 4, 339-356.
Fujita et al., BioorgMed Chem, 2002, 10, 3113-3122.
Gilbertson et al., Tetrahedron Lett, 2002, 43, 6961-6965.
Goguen J.D. et al., Methods, 2000, 21, 179-183.
Houghten R.A. et al., Nature, 1991, 354, 84-86.
Kakefuda et al., Bioorg Med Chem, 2002, 10, 1905-1912.
King et al., J Am Chem Soc, 1982, 104, 7108-7122.
Kramer R.A. et al., Eur J Biochem, 2000, 267, 885-893.
Kukkonen M. et al., Mol Microbiol, 2001, 40, 1-16.
Kukkonen M. et al., Mol Microbiol, 2004, 51, 215-225.
Kutyrev V. et al., Infect Immunol, 1999, 67, 1359-1367.
Lahteenmaki K. et al., FEMS Microbiol Rev, 1995, 25, 531-552.
Lahteenmaki K. et al., Infect Immun, 1998, 66, 5755-5762.
Lahteenmaki K. et al., FEBS Lett, 2001, 504, 69-72.
Lam K.S. et al., Chem Rev, 1997, 97, 411-448.
Lathem W.W. et al., Science, 2007, 315, 509-513.
Mason et al., Current Opinion in Structural Biology, 2003, 13, 526-532.
Masquein et al., Helvet Chim Acta, 1998, 81, 646-660.
McDonough K.A. et al., Mol Microbiol, 1989, 3, 767-775.
Miyaura et al., Chem Rev, 1995, 95, 2457-2483.
Perry R.D., Clin Microbiol Rev, 1997, 10, 35-66.
Quan et al., J Med Chem, 1999, 42, 2752-2759.
Rosse G. et al., J Comb Chem, 2000, 43, 305-341.
Sagan et al., Current Med Chem, 2004, 11, 2799-2822.
Sebbane F., Proc Natl Acad Sci US, 2006, A103, 5526-5530.
Sodeinde O.A. et al., Infect Immun, 1988, 56, 2743-2748.
Sodeinde O.A. et al., Science, 1992, 258, 1004-1007.
Sodeinde O.A. et al., Infect Immun, 1989, 57, 1517-1523.
Sodeinde O.A. et al., Infect Immun, 1988, 56, 2749-2752.
Vandeputte-Rutten L. et al., Embo J, 2001, 20, 5033-5039.
Welkos S.L. et al., Methods Enzymol, 1994, 235, 29-39.
Welkos S.L. et al., Microb Pathogen, 1997, 23, 221-223.
Yamane et al., Synthesis, 2004, 2825-2832.
Zemla A., Nucleis Acids Res, 2003, 31, 3370-3374.

(Continued)

*Primary Examiner* — David Lukton

(74) *Attorney, Agent, or Firm* — Norton Rose Fulbright US LLP

(57) ABSTRACT

The present invention is directed to peptide sequences that were identified from combinatorial libraries and could serve as substrates of plague plasminogen activator (Pla). Another aspect of the present invention is drawn to peptides derived from the substrates for Pla as a result of chemical modifications leading to specific inactivation of the proteolytic activity of Pla. Additionally, the present invention is directed to the use of the substrates identified herein in the detection of bacteria expressing omptin family of proteases which includes *Y. pestis*. Furthermore, the present invention is also directed to the use of the inhibitors identified herein in the prevention and treatment of infection caused by these bacteria.

5 Claims, 18 Drawing Sheets

(56) References Cited

OTHER PUBLICATIONS

Zhang et al., J Biomol Screen, 1999, 4, 67-73.

Agorkov, Bioorganic & Medicinal Chemistry Letters 18, 427-431, 2008.

Dekker, Biochem 40, 1694-1701, 2001.

Kukkonen Maini (International Journal of Medical Microbiology: IJMM 294(1), 7-14, 2004.

Mangel W.F. (Methods in Enzymology 244, 384-399, 1994).

Yun, Blood 113(5), 1139-1148, 2009.

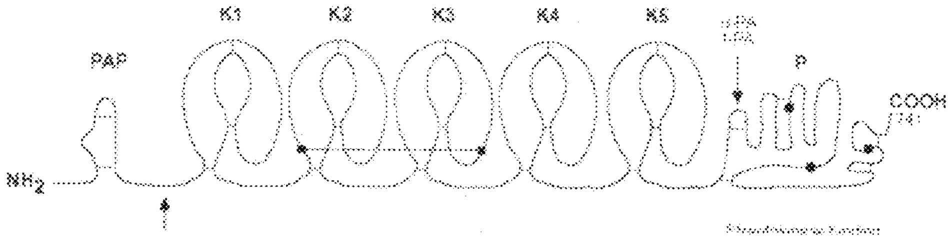
Native human Plasminogen :
(SEQ ID NO: 1)
Lys-Lys-Cys-Pro-Gly-Arg-Val-Val-Gly-Gly-Cys-Val-Ala-His
Endogenous plasminogen activator
$Arg^{560}$-$Val^{561}$
Bovine Plasminogen: (SEQ ID NO: 2)
Lys-Lys-Cys-Ser-Gly-Arg-Ile-Val-Val-Gly-Gly-Cys-Val-Ser-Lys
FIG. 1A
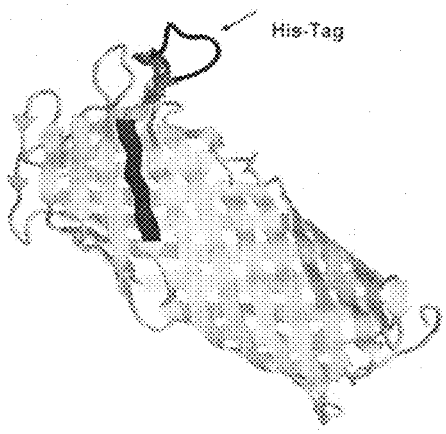
FIG. 1B
Pla: KSHEMLYDAET..........GRKISQLDWKIKN (SEQ ID NO: 3)
Pla+tag: KSHEMLYDAETGHHHHHHGRKISQLDWKIKN (SEQ ID NO: 3)
FIG. 1C

| SEQ ID NO: | | Substrate | Inhibitor |
|---|---|---|---|
| 5 | DABCYL – Arg – Arg – Ile – Asn – Arg – Glu- (EDANS)-$NH_2$ | + | + |
| 6 | DABCYL – Arg – Arg – Ile – Asn – Arg - OH | + | - |
| 7 | DABCYL – Arg – Arg – Ile – Asn - OH | + | - |
| 8 | DABCYL – Arg – Arg – Ile - OH | + | - |
| | DABCYL – Arg – Arg - OH | - | - |
| 9 | DABCYL – Arg – Arg – Ile – Asn – Arg – Gln- EDANS | + | + |
| 10 | DABCYL – Arg – Arg – Ile – Asn – Arg – Gln -$NH_2$ | + | - |
| 11 | pABA – Arg – Arg – Ile – Asn – Arg – Gln- EDANS | + | - |
| 12 | DABCYL – Arg – Arg – Ile – Asn – (EDANS)-$NH_2$ | + | + |
| 13 | DABCYL – Arg – Arg – Ile – (EDANS)-$NH_2$ | + | + |

(24) thio analog

(25) (26) (27) (28) (29) (30)

(30) (31) (32) (33) (34) (35) (36) (37)

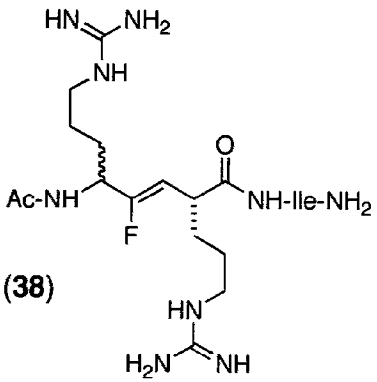
(38)
FIG. 13D
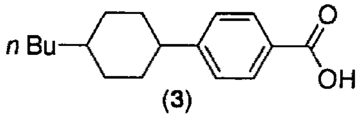
(3)
versus
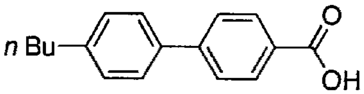
(39)
Sch
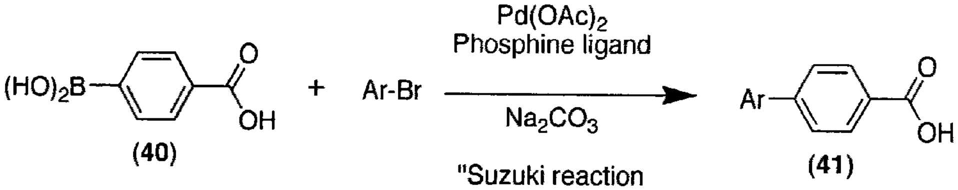
(40) (41)
FIG. 14A
Ar is:
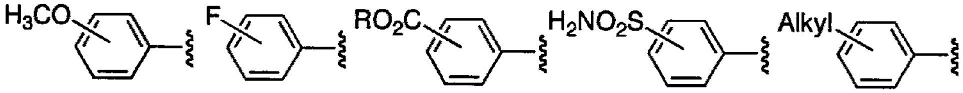
and naphthyl (42)

(43)

(44)

(40)

(45)

(46)

(46) (47) (48) (Is) (49) (50) (51) (52) (53)

R = alkyl or H

(54) (55) (56) (57)

(21) (22)

SUBSTRATE PEPTIDE SEQUENCES FOR PLAGUE PLASMINOGEN ACTIVATOR AND USES THEREOF

CROSS REFERENCE TO RELATED APPLICATION

This is a divisional application under 35 U.S.C. §120 of non-provisional application U.S. Ser. No. 11/901,978, filed Sep. 20, 2007, now U.S. Pat. No. 8,030,447, which claims benefit of priority under 35 U.S.C. §119(e) of provisional application U.S. Ser. No. 60/845,850, filed Sep. 20, 2006, the entirety of both of which are hereby incorporated by reference.

FEDERAL FUNDING LEGEND

This invention was produced in part using funds obtained through grant AI057156 from the National Institutes of Health/National Institute of Allergy and Infectious Diseases. Consequently, the Federal government has certain rights in this invention.

BACKGROUND OF THE INVENTION

1. Field of the Invention

The present invention relates generally to the field of protein chemistry. More specifically, the present invention discloses substrates and inhibitors of plague plasminogen activators and their use in detecting *Yersinia pestis* and controlling the infection caused by *Yersinia pestis*, respectively.

2. Description of the Related Art

*Yersinia pestis*, a Gram-negative bacterium is the causative agent of plague, an acute and lethal disease. Although plague is a zoonotic infection, it could be transmitted to humans via a bite from a flea that previously fed on an infected rodent. Typically, flea transmission of *Yersinia pestis* causes a form of disease referred to as bubonic plague. From the initial site of infection, bacteria disseminate to the draining lymph node, causing swelling of this lymph node to form a bubo, from which, if left untreated, can spread into the circulation, eventually causing bacteremia and the second form of the disease, septicemic plague. Sometimes septicemic disease occurs even without the development of buboes and is characterized by an elevated temperature, chills, headache, malaise and gastrointestinal disturbances.

In addition, pneumonic plague can result if the lungs become infected. Pneumonic plague is the most feared form of the disease that arises due to colonization of the alveolar spaces, and can also be caused by bacterial spread from an infected person (or animal) to a healthy individual by the aerosol route. Pneumonic plague develops rapidly (1-3 days), results in a high mortality rate in infected individuals (approaching 100%), and spreads rapidly from human-to-human. *Yersinia pestis* is responsible for at least three pandemics in the past, killing by estimation more than 200 million people (Perry et al. 1997). For that reason, and because plague is characterized as an emerging infectious disease, the Centers for Disease Control and prevention has classified it as a category A biological agent. For these reasons, the development of highly effective anti-plague treatments, particularly to combat *Yersinia pestis* resistant to traditional drugs is an immediate public health priority.

*Yersinia pestis* contains a unique, 9.5-kb plasmid pPCP that determines four known biochemical functions: a bacteriocin called pesticin, immunity to pesticin and fibrinolytic and coagulase activities. Subsequent studies showed that the latter two activities reside in a single gene encoding an outer membrane protein called plague plasminogen activator (Sodeinde and Goguen., 1988). Plague plasminogen activator expression is associated with the marked ability of *Yersinia pestis* to colonize the viscera and thus cause lethal infection upon administration by peripheral, i.e. intradermal, subcutaneous or intraperitoneal, routes of infection (Sodeinde et al., 1992).

The importance of plasminogen activator for plague pathogenesis was verified with isogenic plasminogen activator mutants of epidemic *Yersinia pestis* strains KIM and CO92, which showed up to $10^6$ logs reduced virulence by the subcutaneous route (Sodeinde et al., 1992; Welkos et al., 1997). Since the plague is transmitted to humans via a fleabite, *Yersinia pestis* exhibits remarkably efficient spreading from the peripheral site of the fleabite to the draining lymph node. This spreading is followed by replication and further invasion of the circulation. The major role in this process has been attributed to plasminogen activator because this plague microbe protease resembles mammalian plasminogen activators in function by converting plasminogen to plasmin by limited proteolysis (Sodeinde and Goguen., 1989), possibly leading to clarification of fibrin deposits that could hinder bacterial migration in circulation (Beesley et al., 1967).

Additionally, it was also shown that plasminogen activator can directly inactivate major plasmin inhibitor α2-antiplasmin (α2AP) (Kukkonen et al., 2001) and mediate adhesion to eukaryotic cells (extracellular matrices and basement membranes) which invasive bacteria must penetrate in order to reach the circulation (Lähteenmäki et al., 1998; Lähteenmäki et al., 2001). Finally, recent work using plasminogen-deficient mice has proven importance of plasminogen activation in the pathogenesis of plague, since such mice had a 100-fold increase in the $LD_{50}$ compared to the normal mice (Goguen et al., 2000). In addition to its role in adhesion, invasion and tissue damage, plasminogen activator has been reported to cleave complement component C3 (Sodeinde et al., 1992), to possess weak coagulase activity (Beesley et al., 1967) and to mediate the proteolysis of *yersinia* virulence factors (Yops) (Sodeinde et al., 1988). Moreover, a significant antibody response to plasminogen activator was induced after experimental plague infection in mice that survived lethal *Yersinia pestis* aerosol challenge following antibiotic treatment (Benner et al., 1999); human convalescent sera from plague patients contained antibodies to plasminogen activator as well (Easterbrook et al., 1995).

The plague plasminogen activator of *Yersinia pestis* is an outer membrane protein, which belongs to the omptin family of bacterial proteases that includes OmpT of *E. coli*, PgtE of *Salmonella* and SopA of *Shigella flexneri* (Lähteenmäki et al., 2001b). However, in contrast to the plague plasminogen activator, the three proteases do not possess the ability either to activate plasminogen or to degrade α2-antiplasmin (Kukkonen et al., 2001), although a recent study suggested that Pgt might have plasminogen-activating capability, which normally stays cryptic for *Salmonella* (Kukkonen et al., 2004). Further, the predicted structure of plasminogen activator is highly similar to that of its OmpT homolog and has a comparitive β-barrel topology with 10 transmembrane β-strands and five surface-exposed loops (Kukkonen et al., 2004). Although plague plasminogen activator is widely referred to as being a serine protease (Lähteenmäki et al., 2001b), the recently resolved structure of homologous OmpT contradicts such a classification (Vandeputte-Rutten et al., 2001). The model predicts that the omptins may constitute a novel class of proteases that is consistent with the observation that commonly used protease inhibitors do not weakly affect the activity of OmpT. Most likely, plague plasminogen activator is not a serine but rather an aspartate protease as predicted for OmpT (Vandeputte-Rutten et al., 2001).

Furthermore, the plasminogen activator protein of *Yersinia pestis* is significantly different from both mammalian plasminogen activators for example, tissue-type and urokinase, which are both serine proteases that are secreted in a single form and processed proteolytically into a fully active two-chain form (Lähteenmäki et al., 2001b). Crystal structures of the catalytic domains of tissue-type plasminogen activator and urokinase plasminogen activator have been resolved; their overall structures exhibit the typical serine proteinase fold, with insertion loops around the active site cleft determining their specificity for plasminogen. Therefore, the mammalian Pas and plague plasminogen activator of *Yersinia pestis* represent a classical case of totally unrelated enzymes that show a similar specificity towards the substrate (plasminogen cleavage resulting in a conversion to plasmin). Thus, compounds inhibiting plasminogen activator activity are unlikely to have any effect on the mammalian blood coagulation system.

Thus, features of plasminogen activator such as its surface location, immunogenicity, the existence of a predicted 3D-model and its involvement in *Yersinia pestis* systemic infection make this protein an excellent candidate to target for development of non-antibiotic therapeutics that are efficacious against plague infection. Despite this, neither substrate specificity nor inhibitors have been found or predicted for the plasminogen activator enzyme.

Thus, prior art is deficient in the knowledge regarding specific substrates and inhibitors of plague plasminogen activator and their use in the detection of *Yersinia pestis* and in the treatment of *Yersinia pestis* infection, respectively. The current invention fulfils this long-standing need in the art.

SUMMARY OF THE INVENTION

The present invention directed to a substrate specific for the omptin family of bacterial proteases. Such a substrate comprises an amino acid sequence with 3 to about 6 amino acid residues, where the N-terminal residue is modified with a quencher or the C-terminal residues is modified with a fluorophore or a combination thereof. The present invention is also directed to a method of detecting an enzymatic activity of omptin family of bacterial proteases. Such a method comprises contacting a cell with the substrate described supra; and measuring cleavage of the substrate by the protease, thereby detecting the enzymatic activity of omptin family of bacterial proteases.

The present invention is further directed to an inhibitor of the omptin family of bacterial proteases. A representative inhibitor comprises the N- and C-terminally modified substrate described supra. Such a substrate has one or more further modifications comprising: a methylated N-terminal residue, D-amino acids inplace of L-amino acids, Lys-Lys or His-His motif inplace of Arg-Arg motif, nitro, methyl, hydroxyl, sulfonyl or benzoyl groups in place of guanidyl moiety of arginine or isoteric analog of the substrate. Additionally, the inhibitor may also comprise compounds 1-22 or analogs or derivatives thereof.

The present invention is further directed to a pharmaceutical composition. Such a composition comprises one or more of the inhibitors described supra and a pharmacologically acceptable carrier. The present invention is further yet directed to a method of inhibiting the enzymatic activity of omptin family of bacterial proteases. This method comprises administering the pharmacological composition described supra.

The present invention is also directed to a method for identifying an inhibitor of the omptin family of bacterial proteases. This method comprises designing a test compound based on compounds 1-22 as lead compounds and measuring a level of cleavage of substrate of the omptin family of bacterial proteases in the presence and the absence of the test compound. The level of the cleavage of the substrate in the presence of the test compound is compared with the level of the cleavage in the absence of the test compound, where a decrease in level of cleavage in the presence of the test compound is indicative that the test compound is an inhibitor of the omptin family of bacterial proteases. The present invention is also directed to the inhibitor identified by the above-discussed method. The present invention is further directed to a diagnostic kit. This kit comprises one or more of the substrates described supra.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIGS. 1A-1C show structure and sequence of plasminogen activator. FIG. 1A shows the domain structure of the human plasminogen molecule. The human plasminogen molecule comprises a pre-activation peptide (PAP), Kringle domains, and a protease domain. The endogenous plasminogen activator cleaves the native human plasminogen at a site between $Arg^{560}$ and $Val^{561}$. Also shown in FIG. 1A is the amino acid sequence of native human plasminogen (SEQ ID NO: 1) and bovine plasminogen (SEQ ID NO: 2). FIG. 1B shows a 3D-model of plague plasminogen activator from *Yersinia pestis* with internal Histidine-Tag inserted into L1 loop after amino acid T36. FIG. 1C shows the alignment of L1 loops of native (SEQ ID NO: 3) and tagged plague plasminogen activator (SEQ ID NO: 4) sequences. The flexible region (potential candidate for His-Tag insertion) marked in red. 3D models were built using LGA algorithm with temperature factor of the atom coordinates determined under conditions of 1M NaCl at neutral pH.

FIG. 2A shows overlapping 6 residue peptides that was used to analyze the loop 5 sequence. FIG. 2B shows the scheme used to profile plasminogen activator protease specificity using combinatorial fluorogenic substrate libraries. The amino acids (underlined) in the scheme are the amino acids that resulted in preferred cleavage of the substrate.

FIG. 8 shows substrate and inhibitory activity of the variations of the hexapeptide substrate. The position of the cleavage site is marked by the arrow. The vertical line designates that the substrates were cleaved by plasminogen activator (LC-MS tested). The inhibitory activity of the peptides was determined using functional assay on fibrin plates.

FIGS. 13A-13D show modifications of the peptide-based molecule to determine the functional groups neccesary for its activity. FIG. 13A illustrates arginine derivatives discussed herein.

FIG. 13B illustrates scheme 2 for the isosteric replacement of the peptide bonds in the substrate. FIG. 13C illustrates scheme 3 for the isosteric replacement of the peptide bonds in the substrate. FIG. 13D shows structure of the direct isosteric analog of the lead peptide.

FIGS. 14A-14C show cyclohexylbenzene and biscyclohexyl hits. FIG. 14A shows biphenyl derivatives of compound 3 (scheme 4). FIG. 14B shows derivation of compound 43 from compound 42 (scheme 5). FIG. 14C shows derivation of compound 46 from compound 44.

FIG. 15A shows derivatives of compound 46. FIG. 15B shows derivatives of compound 54.

DETAILED DESCRIPTION OF THE INVENTION

Figure 2A:
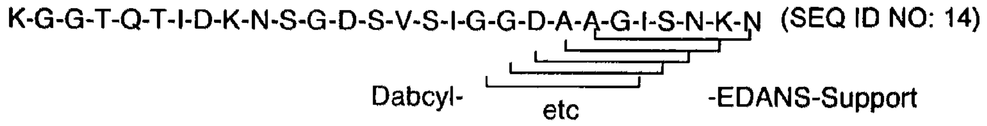
FIG. 2A-2B show sequence of loop 5 (SEQ ID NO: 14) in plasminogen activator and the scheme to analyze this sequence.
Figure 2B:
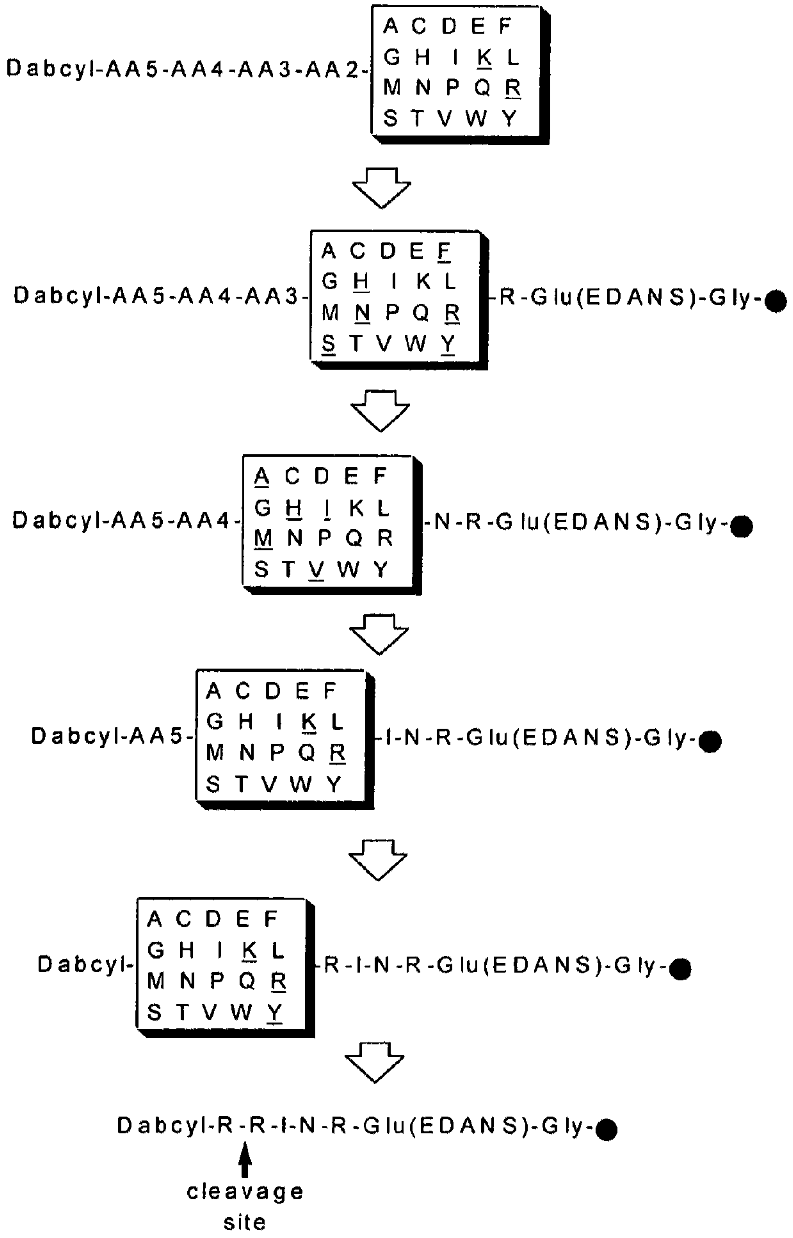

The present invention is drawn to the identification of peptide sequences of plague plasminogen activator. Preliminary studies with the plasminogen activator protein identified regions within the surface-exposed loops of the protein that could be used for the insertion of six histidine residues (His-Tag) (Zemla, 2003). Such an insertion of the internally located His-Tag, without interfering with activity of the enzyme, allows the stretch of histidines outside of the structure to be available for protein-purification purposes using one step of standard $Ni^{2+}$-based affinity chromatography. Using site directed mutagenesis, four different insertions within the distinct areas of the plasminogen activator were constructed and the enzymatic properties of the mutated plasminogen activator were compared with those of the original protein. All testing was done on recombinant plague plasminogen activator expressed in *E. coli* because it is widely recognized that its expression in *E. coli* leads to the appearance of fully functional plasminogen activation activity (Sodeinde and Goguen, 1989; Kukkonen et al., 2001; Kutyrev et al., 1999; McDonough and Falkow, 1989). From the studies of the internally Histidine-Tag-labeled plasminogen activator mutants, it was observed that one of the constructions possessing an insertion into loop L1 after amino acid residue T36 had the properties of the native plague plasminogen activator (FIG. 1). The activities were compared for the ability to convert human Glu-plasminogen to plasmin by kinetic analysis with the chromogenic substrate for plasmin and visualization of Glu-plasminogen time-dependent degradation on silver stained polyacrylamide gel electrophoresisln addition, fibrinolysin assay and cleavage of plasmin inhibitor a2-antiplasmin were employed and proved that the original and Histidine-Tag labeled plague plasminogen activator enzymes were indistinguishable. Using dot-blot with nitrocellulose-immobilized whole cells, it was demonstrated that the Histidine-tag insertions were accessible to anti-$Histidine_6$ antibodies.

The present invention discloses novel peptide substrates for the plasminogen activator. These plasminogen activator protease substrates were identified by screening a combinatorial library of 3.2 million fluorogenic peptide substrates using the positional scan approach as discussed herein. This was followed by mapping of the site of substrate cleavage, which provided crucial information for the design of specific and efficient inhibitors. The sequence of inhibitor design will proceed from peptide-based substrates to peptide-based inhibitors to peptidomimic inhibitors/drugs.

The truncated versions of the hexapeptide were evaluated as substrates and as inhibitors in the fibrinolytic assay. It was possible to reduce the length of substrate to a tetrapeptide DABCYL-Arg-Arg-Ile-Asn-(EDANS)-$NH_2$ (SEQ ID NO: 12) and to a tripeptide DABCYL-Arg-Arg-Ile-(EDANS)-$NH_2$ (SEQ ID NO: 13). Since a tripeptide DABCYL-Arg-Arg-Ile-(EDANS)-$NH_2$ has demonstrated substrate properties similar to those of the hexapeptide DABCYL-Arg-Arg-Ile-Asn-Arg-Glu-(EDANS)-$NH_2$ (SEQ ID NO: 5), further optimization of the tripeptide was under taken. A focused library of tripeptide substrates with Arg-Arg held constant, and the third position varied was screened. Profiling of plague plasminogen activator with this DABCYL-Arg-Arg-X-(EDANS)-$NH_2$ (SEQ ID NO: 15) library revealed a preference for hydrophobic aliphatic (Ala, Ile and Val), neutral-polar side chains (Thr, Ser, and Cys) and small Gly amino acids at that position (FIG. 8). Thus, the optimization of the tripeptide substrate provides a basis for the further development of the substrate-derived inhibitor for plague plasminogen activator.

Alternatively, the present invention contemplates developing inhibitors of plasminogen activator by validating and optimizing compounds selected from small molecule libraries. Briefly, using selected plasminogen activator substrate, 54,100 small molecules at the National Screening Laboratory for the Regional Centers of Excellence in Biodefense and Emerging Infectious Diseases (NSRB) were screened and 124 compounds that possessed the inhibitory activity against plasminogen activator were identified. Small molecule high throughput hits are used herein to develop the inhibitory compound for plasminogen activator.

The advantages of the invention disclosed herein are multifold. Firstly, plasminogen activator protease is a major virulence factor of *Yersinia pestis*, and therefore, inactivation of plasminogen activator by specific inhibitors could be beneficial during the prophylactic and therapeutic treatments of plague infection. Thus, to enable identification of novel non-antibiotic anti-plague agents, the inhibitors of Plasminogen activators discussed supra are examined as prophylactic and therapeutic treatments against plague, either alone or in combination with antibiotics effective against plague infection or in combination with plague vaccination. Different routes of challenge with *Y. pestis*, including aerosol route, are employed. The inhibitors are tested in two animal models suitable for plague infection such as mice and guinea pigs.

Secondly, the substrates and inhibitors of plasminogen activator disclosed herein could possibly act as substrates and inhibitors of other proteases belonging to the same protease family as plasminogen activator (Omptin family of proteases). Therefore, the substrates could be used to determine the enzymatic activity of these proteases, and the inhibitors can control the effect of the microorganisms expressing omptin proteases.

Thirdly, current determination of plasminogen activator activity encompasses indirect techniques which depends on its ability to convert plasminogen to plasmin. There are no technologies describing direct determination of the plasminogen activator activity due to the lack of identified substrates for the plasminogen activator enzyme. There are no known inhibitors of the plasminogen activator protease. *Yersinia pestis* detection could be performed bacteriologically and biochemically, using immunoreactive methods that employ antigen-antibody recognition and using DNA technologies such as Polymerase Chain Reaction (PCR). There are no technologies describing plague microbe detection by using *Yersinia pestis*-specific substrates. The control of plague infection could be achieved by vaccines and antibiotics. There are no *Yersinia pestis*-specific inhitors capable of controlling the effects of *Yersinia pestis*.

Thus, the direct determination of the plasminogen activator enzymatic activity as disclosed by the present invention is more specific than the currently known indirect approach using the reaction of conversion of plasminogen to plasmin since other enzymes (e.g. mammalian tissue plasminogen activator, t-PA, and urokinase, u-PA) can make this plasminogen-to-plasmin transition as well. Moreover, the direct cleavage of the substrate by plasminogen activator occurs in a single step reaction, whereas indirect determination of the plasminogen activator activity requires a two-step reaction. The kinetics of the latter reaction also depends on the relative concentrations of both plasminogen activator and plasminogen in the reaction mixture.

Fourthly, there are no specific plasminogen activator inhibitors availble commercially. Commercial broad-range inhibitors of proteases act weakly on plasminogen activator. *Yersinia pestis* detection by bacteriological and biochemical methods requires pure culture and days of incubation. The immunoreactive methods require specific anti-plague antibodies, and are generally not sensitive unless labeled secondary antibodies and specific devices are used (e.g. ELISA reader). The DNA-based methods require special equipment to perform and detect the reaction (e.g. PCR amplifier device). The detection method based on plasminogen activator substrate is a one-step reaction which takes minutes to complete. The plasminogen activator substrate could be labeled either chromogenically to detect the reaction by eye, or fluorescently to detect the reaction under a UV-lamp.

Fifthly, a plague vaccine for control of *Yersinia pestis* is currently under development. Many antibiotics could be used to treat plague infection; however, these drugs are not plague specific and destroy the normal flora of the patients. Often the treatment with antibiotics themselves could be harmful for the patient. Moreover, multi-drug resistant strains of *Yersinia pestis* have been recently isolated in nature, and such strains could be easily produced by genetic manipulation. The treatment of plague infection with anti-Pla inhibitors discussed herein will be specific to *Yersinia pestis*, therefore, leaving the normal flora intact and being effective against antibiotic-resistant strains of plague.

In one embodiment of the present invention, there is provided a substrate specific for the omptin family of bacterial proteases, comprising: an amino acid sequence with 3 to about 6 amino acid residues, where the N-terminal residue is modified with a quencher or the C-terminal residues is modified with a fluorophore or a combination thereof. Such substrate may be a synthetic peptide or a recombinant peptide. Examples of the quencher may include but is not limited to a 4-(4-dimethylaminophenylazo)benzoic acid, 3-nitro-4-hydroxy-L-phenylalanine or t-butoxycarbonyl and the fluorophore may include but is not limited to 5-(2-aminoethylamino)naphthalene-1-sulfonic acid, aminobenzoyl or (7-methoxycoumarin-4-yl)acetyl. Further, the substrate may have an amino acid sequence of SEQ ID NOS: 5, 6, 7, 8, 9, 10, 11, 12 or 13. Examples of the bacterial proteases may include but is not limited to a plasminogen activator of *Y. pestis*, an OmpT of *E. coli*, a PgtE of *Salmonella* or a SopA of *Shigella flexneri*.

In another related embodiment of the present invention, there is provided a method of detecting an enzymatic activity of omptin family of bacterial proteases, comprising: contacting a cell with the substrate described herein; and measuring cleavage of the substrate by the protease, thereby detecting the enzymatic activity of the omptin family of bacterial proteases. Additionally, the detection may be indicative of diagnosis of infection caused by bacteria expressing the omptin family of bacterial proteases. Further, the enzymatic activity may be detected by assays or methods including but not limited to fluorimetric assay, colorimetric assay or Liquid Chromatography Mass Spectrometry.

In yet another related embodiment of the present invention, there is provided an inhibitor of the omptin family of bacterial proteases, comprising: the N- and C-terminally modified substrate described herein, where the substrate has one or more further modifications comprising: a methylated N-terminal residue, D-amino acids in place of L-amino acids, Lys-Lys or His-His motif in place of Arg-Arg motif, nitro, methyl, hydroxyl, sulfonyl or benzoyl groups in place of guanidyl moiety of arginine or isoteric analog of the substrate; and compounds 1-22 or analogs or derivatives thereof.

In still yet another related embodiment of the present invention, there is provided a pharmaceutical composition, comprising: one or more of the inhibitors described supra and a pharmacologically acceptable carrier.

In another related embodiment of the present invention, there is provided a method of inhibiting the enzymatic activity of the omptin family of bacterial proteases, comprising: administering the pharmacological composition described supra. Such a method may further comprise administering an antibiotic or an immunogenic composition specific for the bacteria. The antibiotic or the immunogenic composition may be administered prior to, concurrent with or subsequent to the pharmacological composition. Additionally, the inhibition of the enzymatic activity may prevent or treat infection caused by bacteria expressing the proteases.

In another embodiment of the present invention, there is provided a method for identifying an inhibitor of the omptin family of bacterial proteases, comprising: designing a test compound based on compounds 1-22 as lead compounds; measuring a level of cleavage of substrate of the omptin family of bacterial proteases in the presence and the absence of the test compound; and comparing the level of the cleavage in the presence of the test compound with the level of the cleavage in the absence of the test compound, where a decrease in level of cleavage in the presence of the test compound is indicative that the test compound is an inhibitor of the omptin family of bacterial proteases. Examples of the bacterial protease may include but is not limited to a plasminogen activator of *Y. pestis*, an OmpT of *E. coli*, a PgtE of *Salmonella* or a SopA of *Shigella flexneri.*

In another embodiment of the present invention, there is provided an inhibitor identified by the method discussed supra. In yet another embodiment of the present invention, there is provided a diagnostic kit, comprising: one or more of the substrate described supra.

As used herein, the term, “a” or “an” may mean one or more. As used herein in the claim(s), when used in conjunction with the word “comprising”, the words “a” or “an” may mean one or more than one. As used herein “another” or “other” may mean at least a second or more of the same or different claim element or components thereof.

As used herein, the term “contacting” refers to any suitable method of bringing the composition described herein into contact with a cell culture system that has been exposed to bacteria. In vitro or ex vivo may be achieved by exposing the above-mentioned cell to the composition in a suitable medium.

As used herein, the term “compound” is interchangeable with “inhibitor”, or “inhibitory compound” and means a molecular entity of natural, semi-synthetic or synthetic origin that blocks, stops, inhibits, and/or suppresses substrate interactions with the omptin family of bacterial proteases.

It is contemplated that the inhibitor compounds described herein may be useful as lead compounds in the design of derivative and analog compounds, including computer-aided design. Alternatively, screening chemical libraries may be screened for structurally similar substituted compounds or analogs, as is known in the art. Potential compounds may be synthesized using the methods described herein or other chemical synthetic methods suitable for the proposed structures. Efficacy of these designed test compounds may be determined using the assays described herein or other assays suitable to determine activity of the omptin family of bacterial proteases. In addition the therapeutic index of the identified inhibitors may be determined by standard methods known to those skilled in the art.

An antibiotic or an immunogenic composition may be administered concurrently or sequentially with the composition used herein. The effect of co-administration with the composition is to treat or prevent the infection. The composition described herein, the antibiotic, or immunogenic composition, or combination thereof can be administered independently, either systemically or locally, by any method standard in the art, for example, subcutaneously, intravenously, parenterally, intraperitoneally, intradermally, intramuscularly, topically, enterally, rectally, nasally, buccally, vaginally or by inhalation spray, by drug pump or contained within transdermal patch or an implant. Dosage formulations of the composition described herein may comprise conventional non-toxic, physiologically or pharmaceutically acceptable carriers or vehicles suitable for the method of administration and are well known to an individual having ordinary skill in this art.

The composition described herein, the antibiotic or the immunogenic composition or combination thereof may be administered independently one or more times to achieve, maintain or improve upon a therapeutic effect. Generally, the composition is administered to the individual at a dose from about 0.1 mg to about 100 mg. It is well within the skill of an artisan to determine dosage or whether a suitable dosage of either or both of the composition and anti-cancer agent comprises a single administered dose or multiple administered doses. An appropriate dosage depends on the subject’s health, the inhibition of the inflammatory genes and/or treatment of the cancer, the route of administration and the formulation used.

As is known to one of skill in the art the immunogenic composition described herein may be administered along with any of the known pharmacologically acceptable carriers. Additionally the immunogenic composition can be administered via any of the known routes of administration such as subcutaneous, intranasal or mucosal. Furthermore, the dosage of the composition to be administered can be determined by performing experiments as is known to one of skill in the art.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

Example 1

Labeling Plasminogen Activator with Internal Affinity Tag

Previously, known aspartic protease inhibitors were tested for their ability to block Pla activity. Examples of such inhibitors comprised a reversible inhibitor of aspartic proteases such as pepstatin A that inhibits cathepsin D, pepsin, renin and HIV-1 protease, inhibitor of pepsin that inhibits HIV protease and an inhibitor of renin. The inhibition assay was done using protocol of Enzolyte HIV-1 Protease assay kit (AnaSpec Corp. San Jose, Calif.). It was observed that the aspartic protease inhibitors tested did not block plasminogen activator activity.

Based on the sequence of human plasminogen, it was known that activation of plasminogen into plasmin occurs when plasminogen activators (t-PA, u-PA) cleave a unique bond between $Arg^{560}$ and $Val^{561}$ in the serine protease domain of human plasminogen resulting in two polypeptide chain, linked to each other via two disulphide bonds (FIG. 1). However, the mammalian PAs and Pla of *Y. pestis* are unrelated enzymes that show similar specificity towards substrate. It was observed that the sequence derived from the cleavage site of human plasminogen activator did not serve as a substrate for plague plasminogen activator.

A topology model for Pla was developed and the regions within the surface-exposed loops of the protein that could be used for the insertion of a stretch of six histidine residues (His-Tag) were identified. Such an insertion of the internally located His-Tag, without interfering with the activity of the enzyme, will allow the stretch of histidines to be exposed outside of the structure to be available for protein purification purposes, using one step of standard, $Ni^{2+}$-based affinity chromatography. Using site-directed mutagenesis, four different insertions within the distinct areas of the Pla were constructed and the enzymatic activities of the mutated Pla with those of the original protein were compared. All testing was done on recombinant Pla expressed in *E. coli*, because it is recognized that its expression in *E. coli* leads to the appearance of fully functional plasminogen activation activity (Sodeinde and Goguen, 1989; Kukkonen et al., 2001; Kutyrev et al., 1999; McDonough and Falkow, 1989). From studies of the activity of internally His-Tag-labeled Pla mutants, it was shown that one of the constructions possessing an insertion into loop L1 after amino aid residue T36 (FIGS. 1B and 1C) had the properties of native Pla.

The activities were compared for the ability to convert human Glu-plasminogen to plasmin by kinetic analysis with the chromogenic substrate for plasmin and visualization of Glu-plasminogen time-dependent degradation on silver-stained PAGE. In addition, fibrinolysin assay and cleavage of the plasmin inhibitor _2-antiplasmin were employed and proved that the original and His-Tag labeled Pla enzymes were indistinguishable. Using dot-blot with nitrocellulose-immobilized whole cells, it was shown that His-Tag insertions were accessible to anti-$His_6$ antibodies (Novagen). The His-Tag labeled Pla was purified by Ni-affinity chromatography and used for testing of Pla-specific substrate and to evaluate the inhibitory reactions.

Example 2

Profiling of Plasminogen Activator Protease Specificity Using Combinatorial Fluorogenic Substrate Libraries Initially a mixture of 3.2 million fluorogenic peptides where synthesized and screened in solution. After determining that small peptides ≤6 residues can serve as substrates the positional scan approach reported by Houghten was used to identify individual peptides (Houghten et al., 1991). In this approach one amino acid position is held constant while the others are varied. The Fmoc-Glu(EDANS)-Gly-Wang resin was divided into 20 equal portions, and each portion was coupled to an individual amino acid followed by coupling with an isokinetic mixture of eighteen amino acids (excluding cystine and hystidine) and then the final introduction of Dabcyl. This provides each vessel with a mixture of dimers with the known amino acid at position 1 and all other twenty amino acids represented at position 2. This process is then repeated for positions 3, 4 and 5.

Each well is then tested in kinetic reaction with Pla to determine which amino acid in the first position gives the best result. Fluorescence was detected using a plate reader at excitation and emission wavelengths of 360 and 460 nm, respectively. This amino acid is then held constant and the second position is then scanned in the same manner as the first. Those 20 vessels are then tested and a decision is made as to which amino acid is best in the second position. This process is then repeated for the third, fourth and fifth positions. In addition to pentamers this process was carried out for tetramers, and trimers. One important issue to be considered when using this system is that different amino acids may couple at different rates. This potential problem is addressed by using an isokinetic mixture where the ratios of the amino acids are adjusted in the mixture to account for the differences in reaction rate between the individual amino acids.

Scheme 1 illustrates the process. The amino acids that are underlined are amino acids that resulted in preferred cleavage of the substrate. Ultimately, based on qualitative differences in the rate of cleavage between different active sequences, DABCYL-Arg-Arg-Ile-Asn-Arg-Glu-(EDANS)-$NH_2$ was selected as the substrate candidate for Pla.

Example 3

Kinetic Characterization of Identified Plasminogen Activator Substrate

Figure 3:
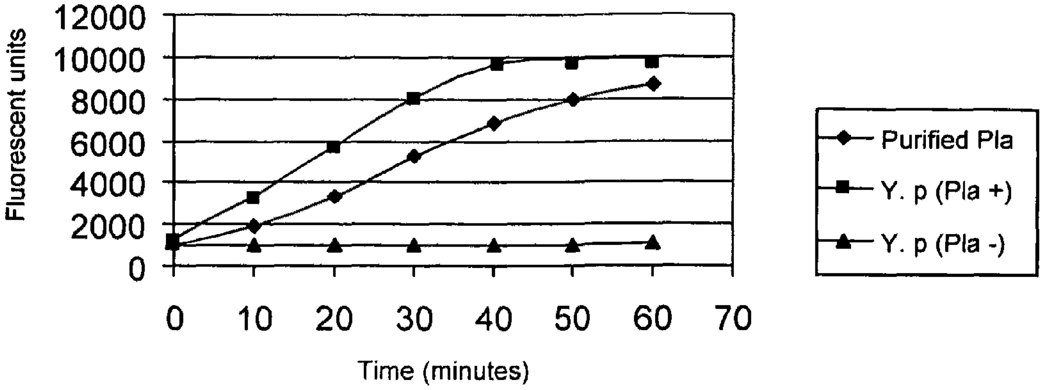
FIG. 3 shows the kinetics of cleavage of identified fluorescent substrate by plague plasminogen activator. The activity was measured with purified recombinant plague plasminogen activator (purified Pla) ♦, *Yersinia pestis* cells expressing plague plasminogen activator (Y.p (Pla +) ■, and *Yersinia pestis* cells lacking plague plasminogen activator gene (Y.p (Pla −) ▲.

Plasminogen activator activity was measured in a fluorimetric assay using identified substrate DABCYL-Arg-Arg-Ile-Asn-Arg-Glu-(EDANS)-$NH_2$ (SEQ ID NO: 5). In FIG. 3, activity is given as a function of time for both purified recombinant Plasminogen activator and an isogenic pair of *Y. pestis* strains either expressing or not the Plasminogen activator protease on the cell surface. Both purified and cell-associated Pla enzyme cleaved the substrate in a time-dependent way, reaching a plateau in about 60 min. Pla-negative mutant showed low background fluorescence indicating strict substrate specificity towards Pla.Kinetic parameters were determined by measuring Pla activity at 0-54 mM substrate at neutral pH and subsequent fitting of the resulting hyperbolic saturation curve ($K_m$=3×$10^{-5}$ M).

Example 4

Inhibition of Plasminogen Activator Activity by Substrate (Fluorimetric Assay and Functional Assay)

Figure 4A:
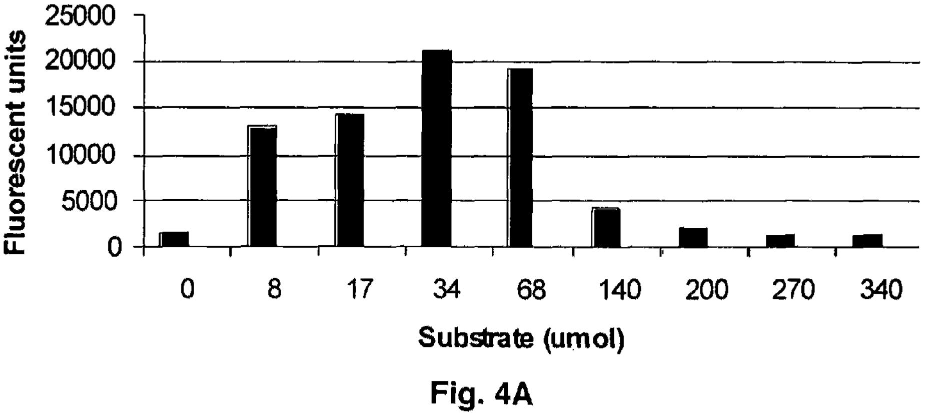
FIGS. 4A-4B show fluorimetric assay of plasminogen activator activity at various substrate concentrations. The activity was measured at the end point of the reaction with purified recombinant plasminogen activator (FIG. 4A) and *Y. pestis* expressing plasminogen activator (FIG. 4B) on their surface.
Figure 4B:
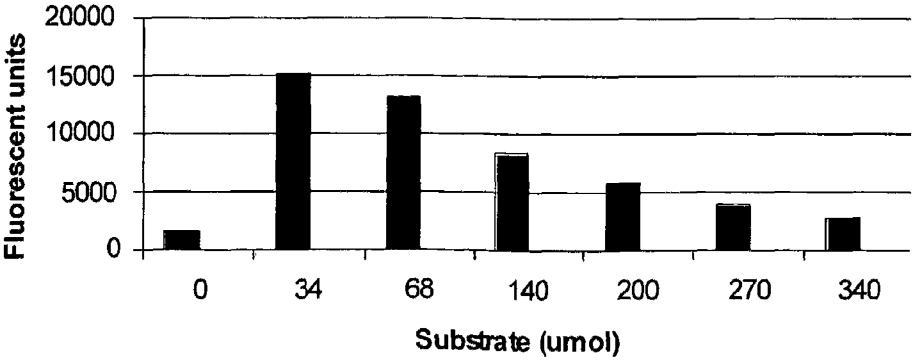

The inhibition of Pla protease was detected by the substrate DABCYL-Arg-Arg-Ile-Asn-Arg-Glu-(EDANS)-$NH_2$ in a fluorimetric assay starting at certain concentrations (>70 mM) when the amount of purified Pla in the reaction remained constant. This finding is illustrated by the data of the representative experiments (FIG. 4A). Importantly, high concentrations of the substrate inhibited not only pure Pla, but also the enzyme expressed on the surface of *Y. pestis* (FIG. 4B). This observation indicates that the proposed approach of developing inhibitors based on this type of substrate has promise.

Figure 5:
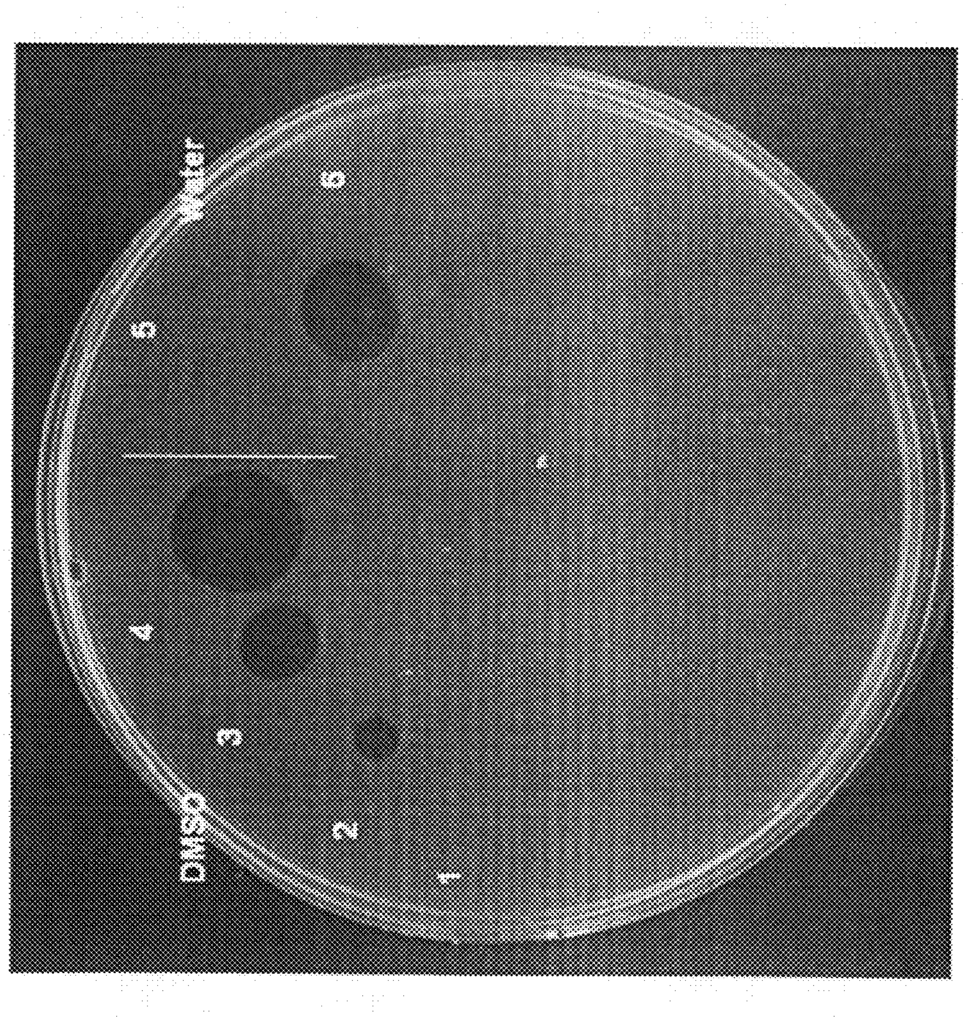
FIG. 5 shows a fibrinolytic assay of plague plasminogen activator activity at various substrate concentrations. The substrate is taken in 2-fold dilutions. Spots 4 and 6 represent the samples with no substrate added. Spots 1, 2, 3 and 5 have different substrate concentrations. The substrate was dissolved either in dimethylsulfoxide or in water.

Plague fibrinolytic factor Pla activates plasminogen to plasmin, resulting in the proteolytic dissolution of fibrin seen as a clear liquid spot on an opalescent fibrin film. Pre-incubation of purified Pla with the substrate DABCYL-Arg-Arg-Ile-Asn-Arg-Glu-(EDANS)-$NH_2$ followed by spotting the samples on the fibrin film resulted in a concentration-dependent inhibition of Pla-mediated fibrinolysis (FIG. 5). Importantly for animal testing, the Pla substrate is water soluble, and capable in this form to inhibit the functional activity of Pla. It was also observed that the substrate of the present invention could inhibit Pla expressed by *Y. pestis* cells in a similar manner, but did not prevent the action of mammalian plasminogen activator urokinase (data not shown)

Example 5

Determination of Cleavage Site for the Selected Pla Substrate

Figure 6A:
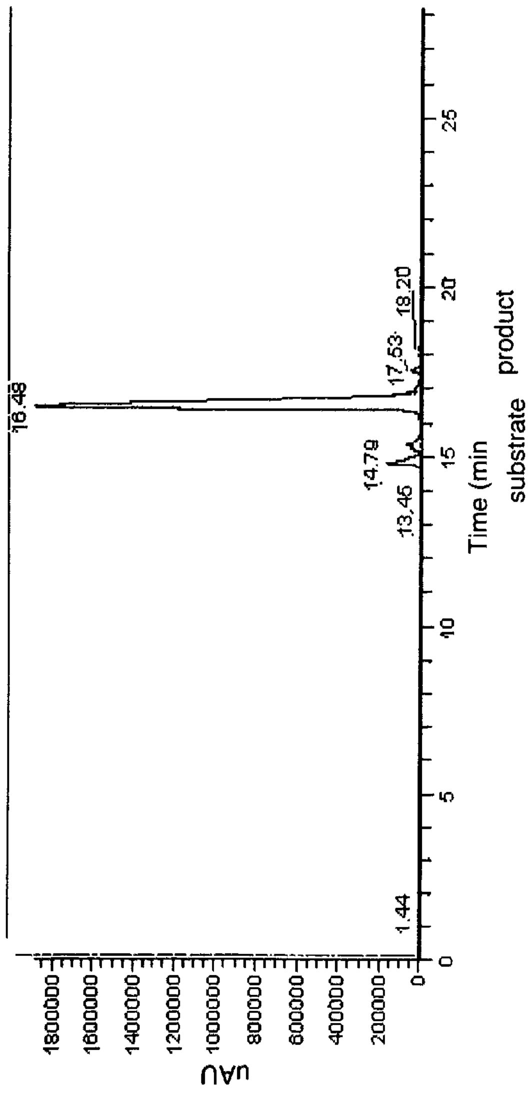
FIGS. 6A-6B show a Liquid Chromatography-Mass Spectrometry Assay (LC-MS) of the substrate prior to incubation with plasminogen activator (FIG. 6A) and after the cleavage by plasminogen activator (FIG. 6B). The peaks for uncleaved (substrate) and completely cleaved (product) of a hexamer substrate are shown.
Figure 6B:
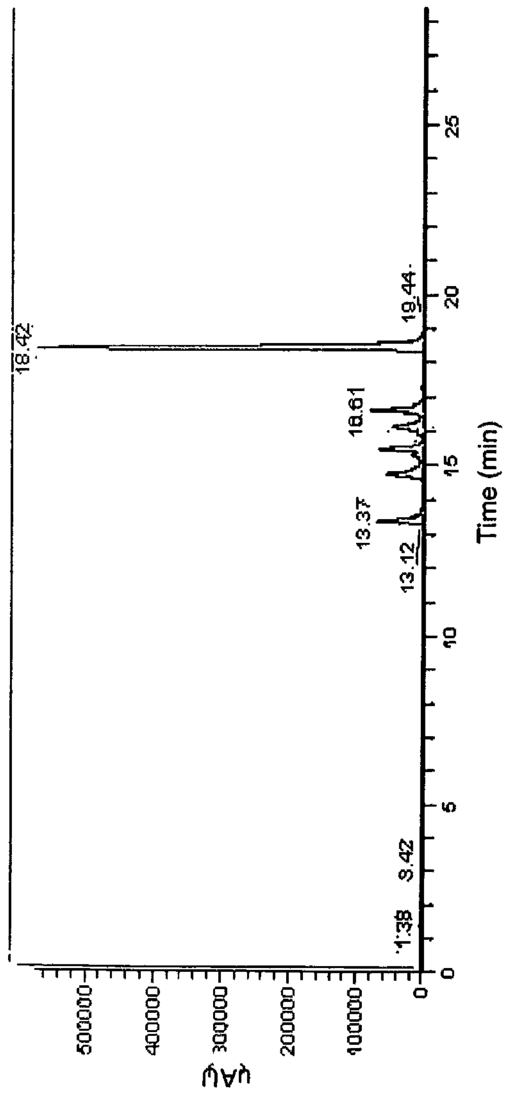

The identification of the site of substrate cleavage by protease is crucial for designing peptide-based inhibitors derived from the peptide-based substrate. To determine the specificity of the Pla enzyme, the identified substrate DABCYL-Arg-Arg-Ile-Asn-Arg-Glu-(EDANS)-$NH_2$ was hydrolyzed with purified recombinant Pla, followed by a Liquid Chromatography-Mass Spectrometry assay (LC-MS). In FIGS. 6A-6B, the peaks corresponding to the original substrate and its cleaved product were eluted at different times. The subsequent MS-analysis identified that Pla cleaves the substrate between two arginines. This observation corresponds well with the substrate specificity of the omptin family of proteases which have a preference to cleave between two basic amino acids (Vandeputte-Rutten et al., 2001).

Example 6

Concentration-dependent Inhibition at Cleavage Site

Figure 7A:
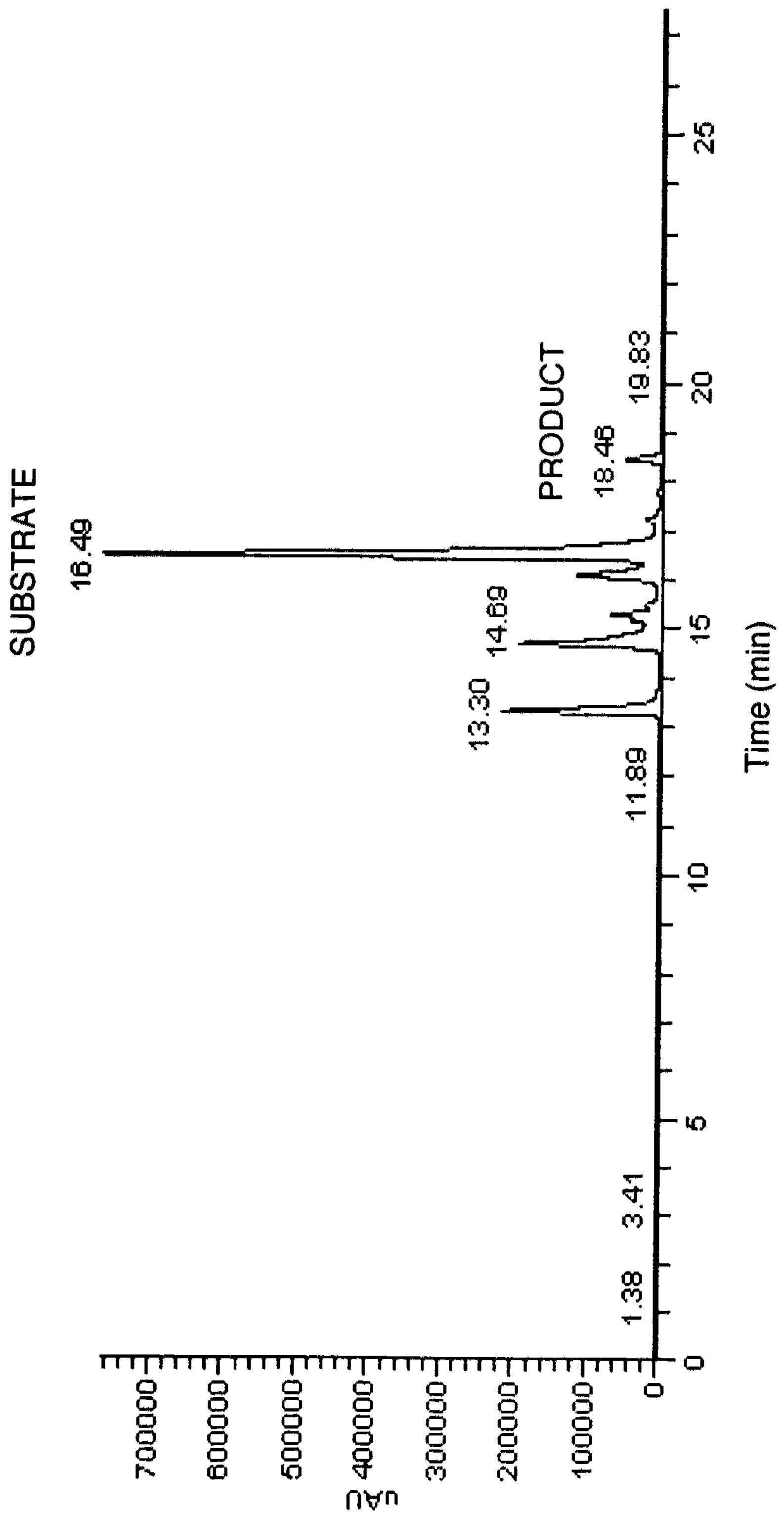
FIGS. 7A-7D show an LC-Chromatogram after incubation of plasminogen activator with the substrate at concentrations of 270 μM (FIG. 7A), 200 μM (FIG. 7B), 140 μM (FIG. 7C) and 68 μM (FIG. 7D). The peaks for uncleaved (substrate) and completely cleaved (product) of the hexamer substrate are shown.
Figure 7B:
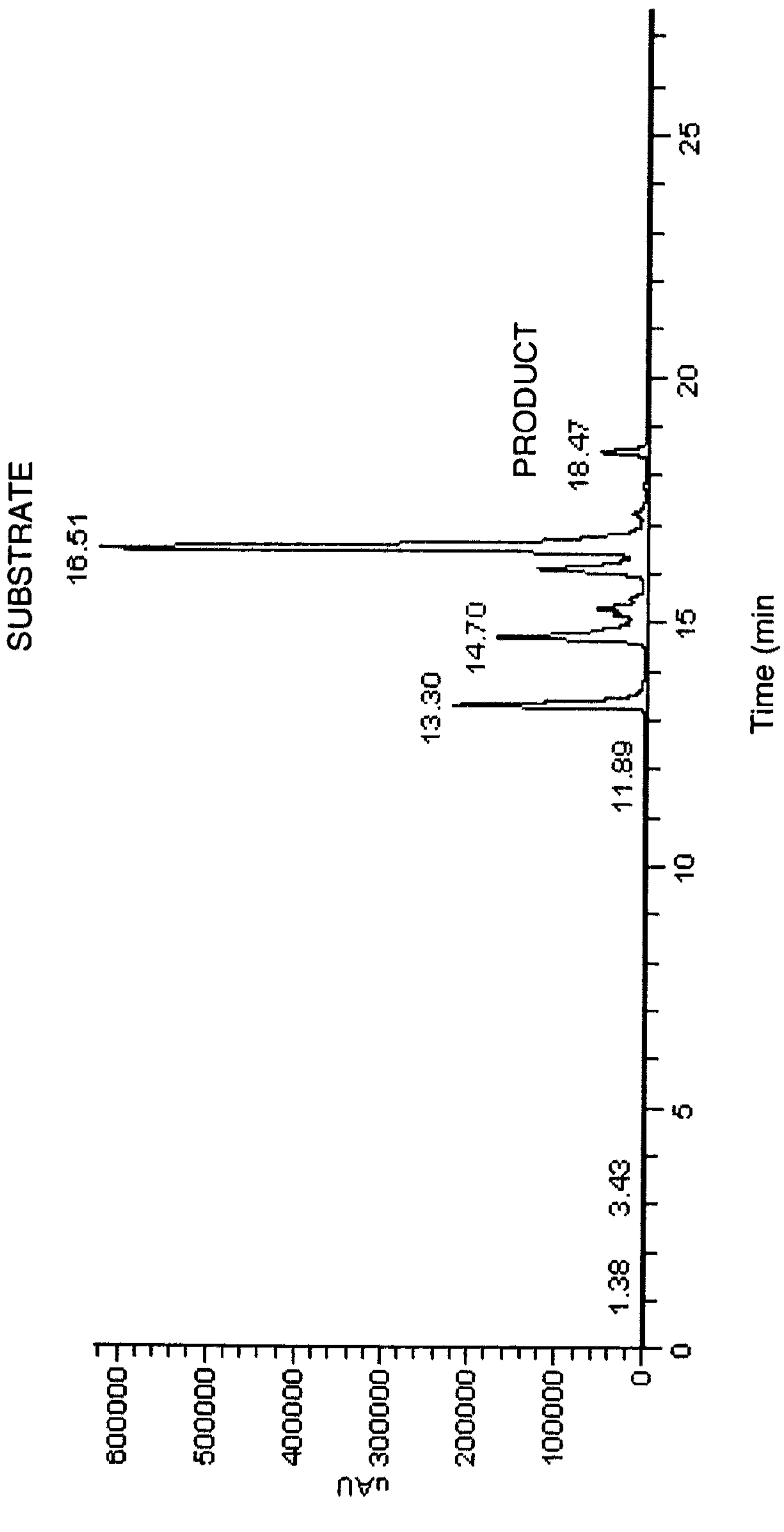
Figure 7C:
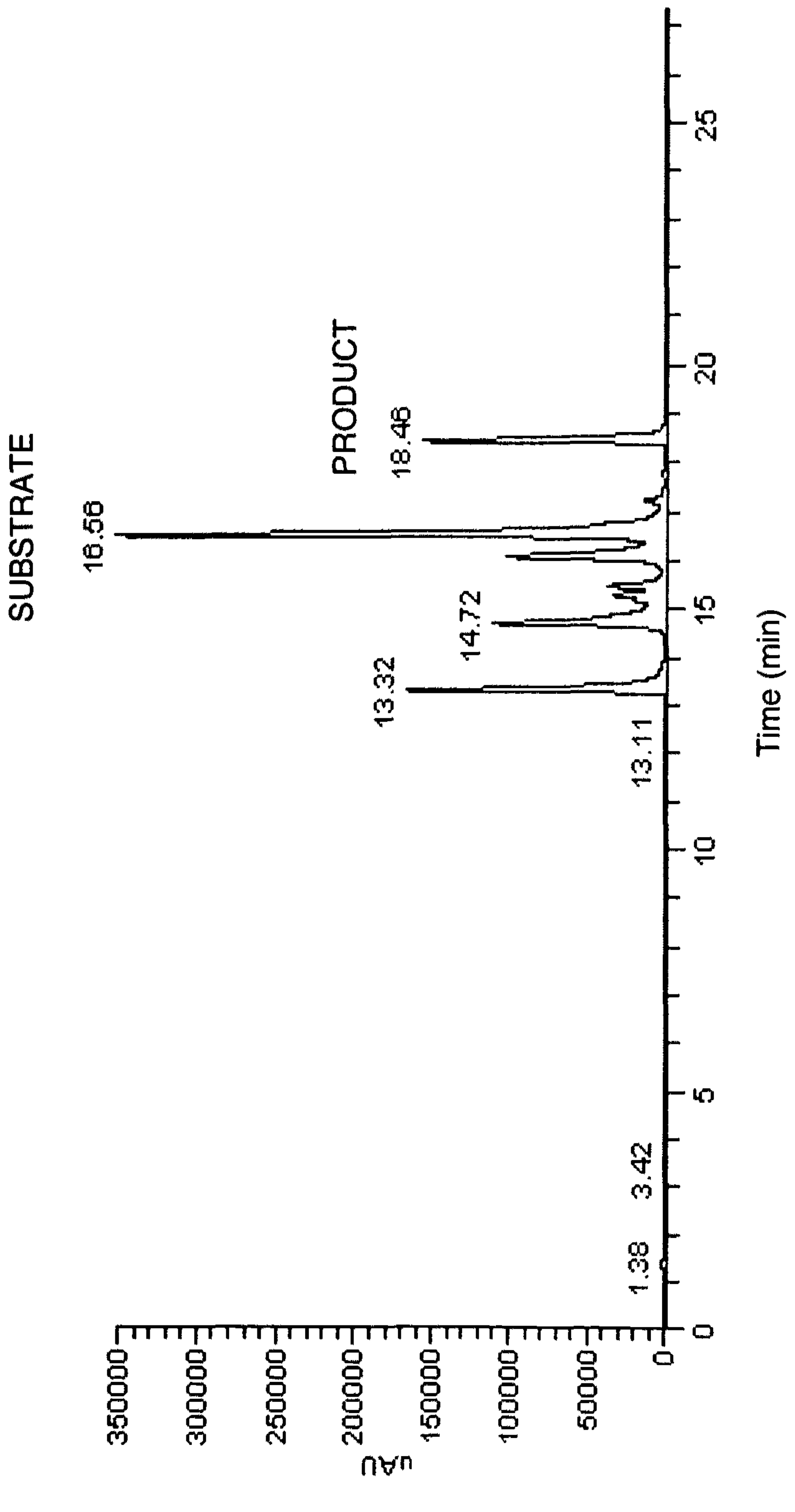
Figure 7D:
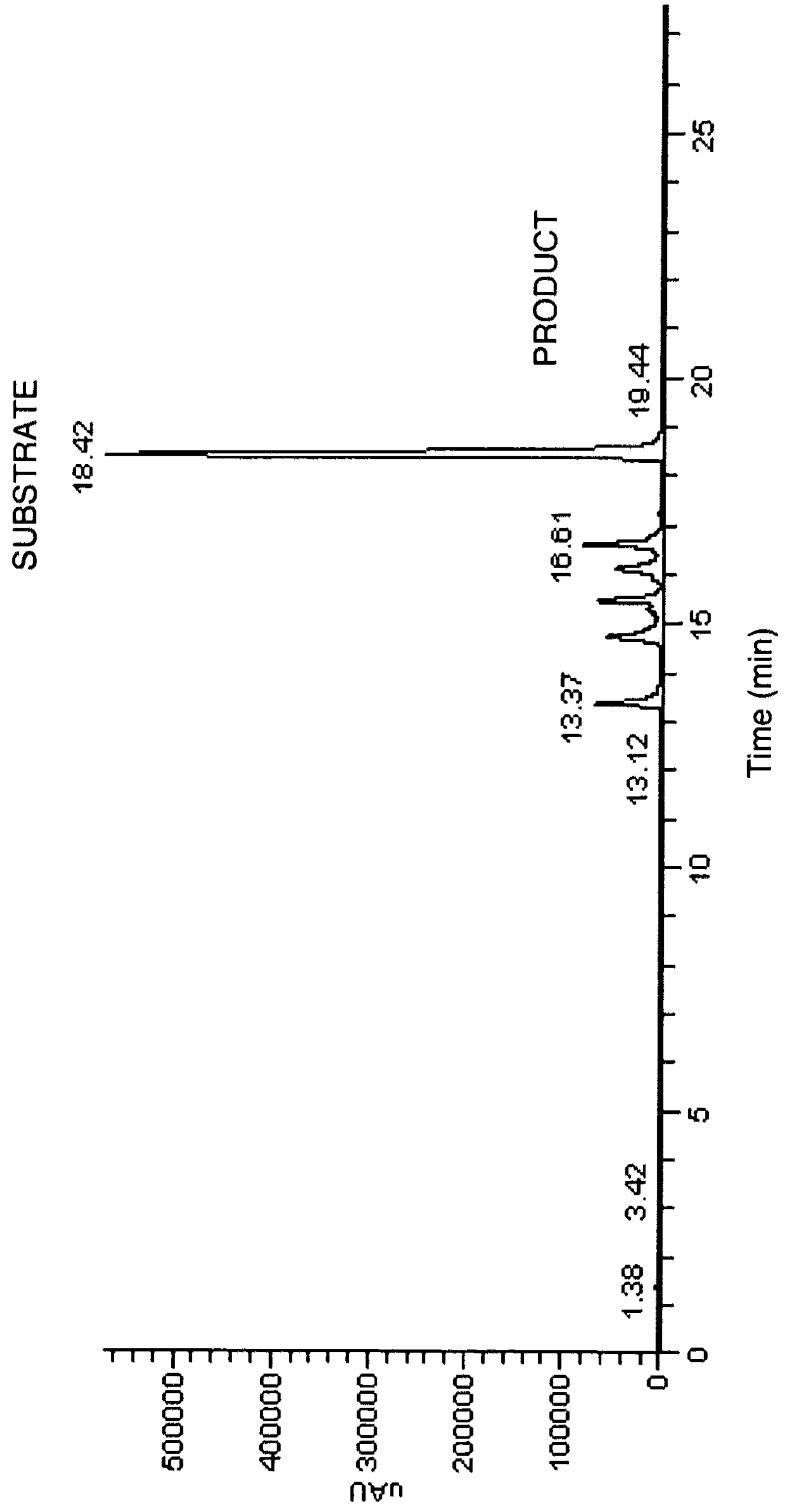

The concentration dependence of inhibition was determined. Substrate cleavage was followed by HPLC at four concentrations. As seen from FIGS. 7A-7D, when the reaction mixture contained 68 mM (FIG. 7D) of the hexapeptide, that substrate was completely cleaved by Pla. In contrast, high concentrations of substrate (≥200 mM; FIGS. 7A-7C)) led to the inhibition of cleavage. While at intermediate amounts, 140 mM of substrate, both peaks corresponding to the cleaved and uncleaved substrate were present.

Example 7

Truncation of the Hexapeptide Substrate

Experiments were carried out to determine the minimum length peptide that could serve as a substrate as well as an inhibitor for Pla. In addition the role of the fluorophore on inhibition and the ability of peptide to serve as a substrate was evaluated. The truncated versions of the hexapeptide substrate with and without the EDANS group were evaluated as substrates and as inhibitors in the fibrinolytic assay. DABCYL-Arg-Arg-Ile-Asn-Arg-Glu-(EDANS)-$NH_2$ were synthesized without a fluorophore EDANS but with the quencher DABCYL, followed by testing of their inhibitory activity using a fibrinolytic assay. Peptides lacking the EDANS were not inhibitors although LC-MS assay showed that all, except the shortest peptide DABCYL-Arg-Arg-OH were cleaved by Pla (FIG. 8). The results of this experiment indicated that EDANS plays a role in increasing inhibitory activity. It was also shown that EDANS can be attached by either the side chain or main chain carboxyl and maintain activity (FIG. 8). Synthesis of the hexapeptide omitting either EDANS or DABCYL resulted in loss of the inhibitory activity, indicating that both fluorophore and quencher are important for the inhibition of Pla (FIG. 8). Nevertheless, free EDANS and Dabcyl did not inhibit the Pla enzyme (data not shown). Finally, the length of the substrate was reduced to a trimer DABCYL-Arg-Arg-Ile-(EDANS)-$NH_2$ (SEQ ID NO: 13) (FIG. 8) and the activity maintained. Using kinetic characterization and testing inhibition activity by fluorimetric and functional fibrinolytic assays, both tetra- and tri-peptides displayed substrate and inhibitory properties similar to those of the lead hexamer substrate (FIG. 8). This was significant in that this is a smaller peptide and offered enhanced potential as a drug lead.

Example 8

Optimization of the Tripeptide Substrate

Figure 9:
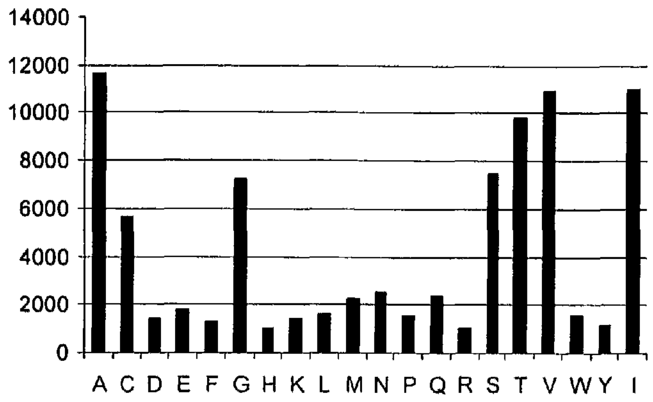
FIG. 9 shows profiling of the tripeptide DABCYL-Arg-Arg-X-(EDANS)-$NH_2$ library. The X represents one of the twenty amino acid residues. The y axis is the end point fluoroscent signal after 2 h of incubation of the substrate with purified plasminogen activator. The x provides the spatial address of the amino acid as represented by the one letter code. Each substrate was used at a concentration of 35 μM.
Figure 10:
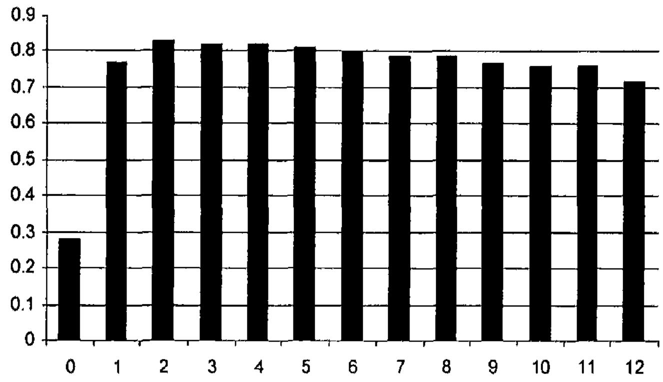
FIG. 10 shows typical Z' values over the 12-hour course of the screen.

Since a tripeptide DABCYL-Arg-Arg-Ile-(EDANS)-$NH_2$ has demonstrated substrate properties similar to those of the hexapeptide DABCYL-Arg-Arg-Ile-Asn-Arg-Glu-(EDANS)-$NH_2$, further optimization of the tripeptide was under taken. A focused library of tripeptide substrates with Arg-Arg held constant, and the third position varied was screened. Profiling of Pla with this DABCYL-Arg-Arg-X-(EDANS)-$NH_2$ library revealed a preference for hydrophobic aliphatic (Ala, Ile and Val), neutral-polar side chains (Thr, Ser, and Cys) and small Gly amino acids at that position (FIG. 9). Thus, the optimization of the tripeptide substrate provides a basis for the further development of the substrate-derived inhibitor for Pla.

Example 9

High-throughput Screening Using Fluorgenic Peptide Substrates 54,100 Compounds from 19 libraries were subjected to the assay protocol. The actual number of compounds tested is approximately 20% lower due to the presence of fluorescent compounds in the collection that interfered with the assay. (Experimental wells with these compounds exhibited fluorescence significantly higher than the positive control at the initial time point.) The measurements were taken every 60 min for 12 hours. Using $23^{rd}$ column on every plate as a positive control (Pla+ and the substrate) and $24^{th}$ column as a negative control (Pla− and the substrate) Z' values were determined for each reading (Zhang et al., 1999). The highest Z' value was usually achieved after 2-3 hours and the absolute value was at least 0.75. A typical set of data is shown below:

The compounds' activities were checked at the maximum Z' value (after 2-3 hours; $3^{rd}$ reading). At this point the positive control typically has shown 5-6 fold increase over the negative control. Hits were generated using following logical function:

IF $[(S-Av_-)/(Av_+-Av_-)\times 100\%]<50\%$ is TRUE, THEN it is a HIT where S—signal intensity, Av−—negative control average, $Av_+$—positive control average.

Figure 11:
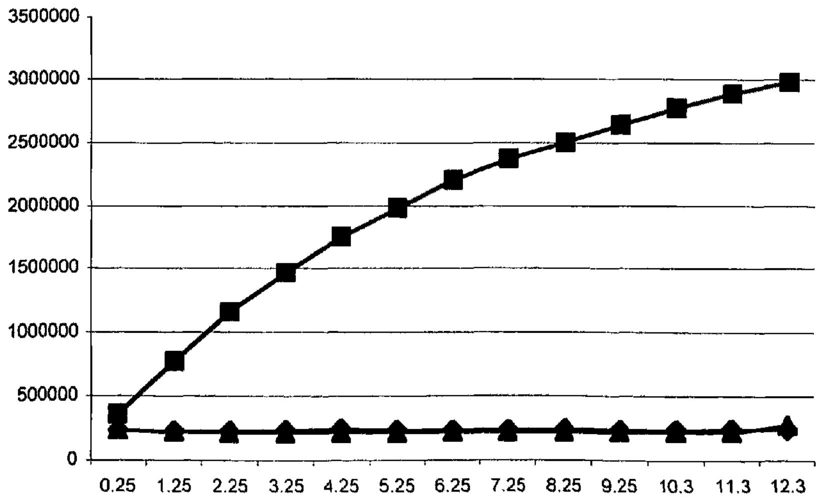
FIG. 11 shows the inhibitory activity for compound 1 where ♦ is 1548_M18, ■ is the positive control and ▲ is the negative control.
Figure 12:
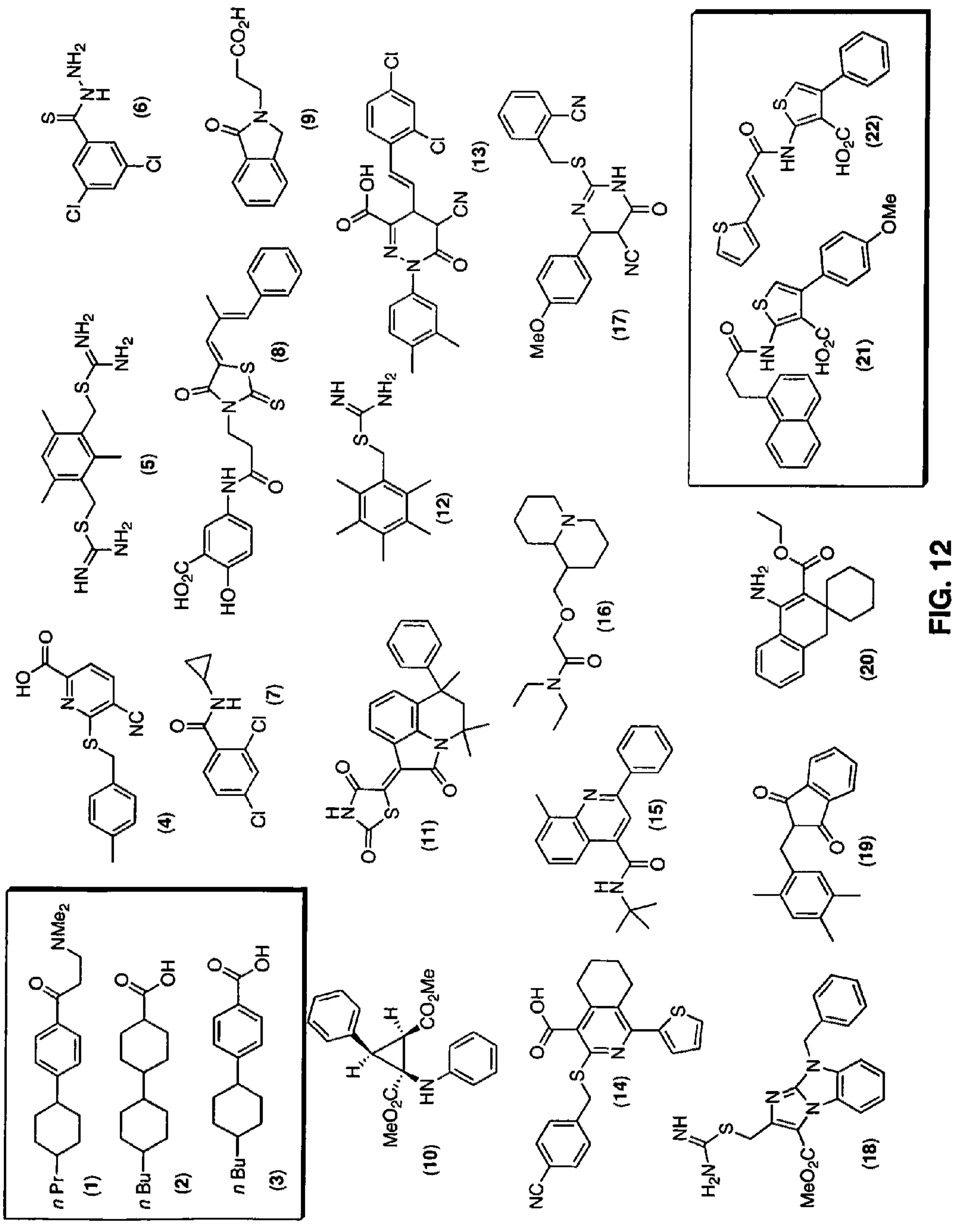
FIG. 12 depicts the structural information for the compounds that showed the strongest inhibitory activity for the plasminogen protease during high-throughput screening.

All compounds with at least 50% decrease in the signal intensity were selected (147 commercial compounds). Then the distribution of wells registering as hits was checked to verify proper operation of the detector and distribution systems. Standard deviations of two readings were determined at this point and 10 hits with standard deviation >500% were eliminated. This analysis produced 124 commercial compounds as hits. The hits can be further ranked according to the determined percent of inhibition. At 3 hours there were 26 compounds within 10% of the negative control (the most potent compounds) and of those 18 remained at that level after 12 hours. FIG. 11 is representative of data obtained for the compounds selected for further study. These compounds are shown in FIG. 12.

Example 10

Design of Novel Peptidomimmic Inhibitors of Plasminogen Activators

Briefly, through a fluorogenic assay, peptides ranging from 3 to 6 amino acids were found to act as substrates for and selective inhibitors of Pla. These peptides are optimized for their ability to selectivity inhibit Pla as well is for their pharmacological properties. The sequence of inhibitor design proceeds from peptide-based substrates to peptide-based inhibitors to peptidomimic inhibitors/drugs. The typical problems with peptide-based drugs are stability against proteases, due to the amide bonds, and poor pharmacokinetic properties, due to their polar nature. Both of these issues are considered in the development of inhibitors based on these molecules. While a number of approaches are proposed to optimize the peptides, the first issues that are addressed are replacement of the hydrolytically labile Arg-Arg amide bond and improvement of the pharmacological properties of the very polar guanidine side chains.

Probing the Role of the EDANS and DABCYL Group

The small tripeptides containing the EDANS and DABCYL groups were found to act as inhibitors and that the corresponding peptides without these groups are substrates but not inhibitors at the same concentrations. Along those lines, a group of peptides that have molecules with similar structures to those of the EDANS and DABCYL are synthesized and tested. To probe the role of EDANS, sets of peptides with, naphthylene, a benzene sulfonic acid as well as a simple benzene ring and an alkyl chain replacing of EDANS are synthesized and tested. The goal of this work is to determine if the role of EDANS is that of a hydrophobic group or if the sulfonic acid is important. If the EDANS group proves to be necessary, then the other feature that is examined is the length of the tether between the fluorophore and Glu side chain.

The original Glu-EDANS moiety has two methylenes between the acid side chain of Glu and the naphthylene-sulfonic acid. Glu-EDANS motifs is synthesized, with the length of the tether varied, and its rigidity modified (phenyl as a tether). Such molecules are readily available from commercially available diamines. In the case of the DABCYL group the same type of approach is taken. The diaryl diazene will be replaced with groups such as diaryl ethers with a par-dimethylamino group on the terminal benzene ring. Additionally, the N═N of the diazene will be replaced with a C═C bond. The necessary stilbenes for this substitution are commercially available. The determination of the importance of the EDANS and DABCYL groups is pivotal in the course of designing the inhibitors. If they are found to be necessary, then the subsequent inhibitors will include them. If not necessary, peptides will that do not possess these groups will be used.

Simple Modifications to Peptide Structure

Now that an inhibitor has been found for Pla, the peptide-based molecule are modified to determine what functional groups are necessary for activity. The ultimate goal is to find small nonpeptidic molecules that have high activity and good pharmacological properties. This is accomplished in a number of ways. N-methylation is a standard approach to developing peptide leads that have better stability (Dive et al., 1992; Billich and Zocher, 1990; Mason et al., 2003; Sagan et al., 2004). This approach is synthetically simple and allows for direct analogs to go into animal studies. Another approach that is used easily is the synthesis of the peptide with the L-amino acids replaced by D-amino acids (Fischer, 2003). It is known that mirror image peptide libraries, where the peptides are synthesized in reverse order with L-amino acids rather than D-amino acids, contain peptides with inhibitory activity. Since it has been shown that such peptides have activity, mirror image analogs of the active peptides will be synthesized and tested. This is synthetically very simple to perform and will provide analogs with better in vivo stability that are readily available for animal studies.

Sequences with basic side chains other than the guaninidine of arginine are also examined. Peptides with Lys-Lys and His-His replacing the Arg-Arg motif are tested. It is noteworthy that in the original screen there were active peptides that had Lys in place of Arg at these two sites. There are also a number of different, commercially available arginine derivatives (FIG. 13A), in which nitro, methyl, hydroxyl, sulfonyl and benzoyl groups are substituted for the guanidine.

Figure 13A:
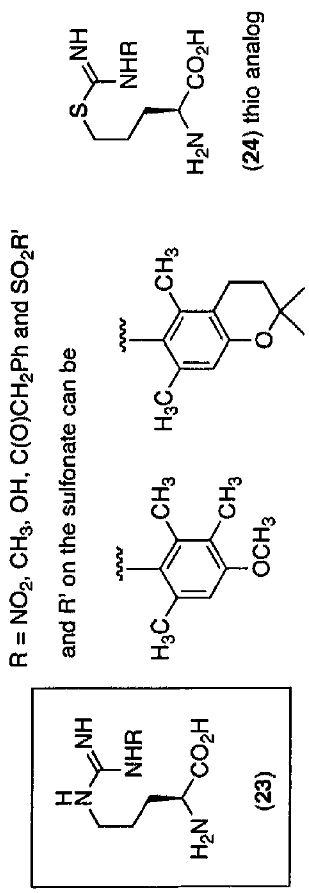
Figure 13B:
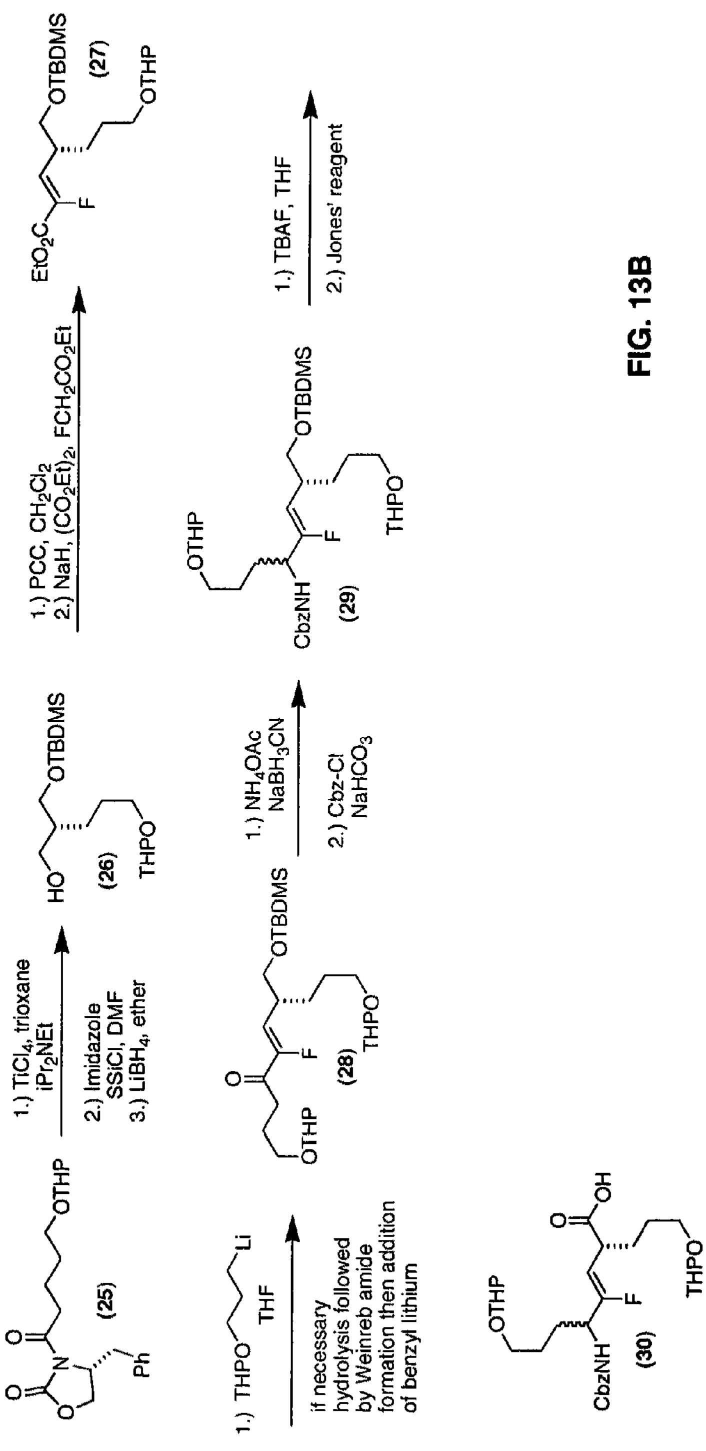

Peptide sequences with these arginines derivatives are examined. In the screening of small molecule libraries (FIG. 12), a number of the hits contained S-alkyl isothioureas (a thio guanidine). For that reason peptide mimics where the guandine side chain replaced by the alkyl isothiourea are also be synthesized and tested (FIG. 13A, compound 24).

Isosteric Replacement of Peptide Bonds

While approaches like N-methylation and mirror-image synthesis can be used to circumvent the problems of in vivo stability against proteases, they are much less effective at improving the pharmacokinetic properties of peptide-based molecules. The ultimate goal is to develop molecules that have drug-like properties, such as good log P values and molecular weights below 500. To accomplish this, some of the amide bonds will need to be replaced with carbon-carbon bonds. The first example of this approach is by substituting an amide equivalent for the peptide bond at the cleavage site, between the two arginines. Scheme 2 presents the route to a fluoro version of an Arg-Arg isostere. This approach represents a modification of the Bartlett work (Bartlett and Otake, 1995). Reaction of the chiral oxazolidinone with trioxane, followed by silylation and reduction gives the differentially protected chiral triol (compound 26). Oxidation and condensation with the fluoroacetic acid provides the a,b-unsaturated fluoro ester (compound 28).

Addition of propyl lithium to either the ester or the Weinreb amide gives a ketone that upon reductive amination and Cbz protection gives (compound 29). Removal of the TBDMS group and oxidation should yield a carbamate-protected acid building block (compound 30) of the type that Bartlett has shown will participate in solid-phase peptide synthesis. While this method provides optically active material, this approach suffers from a lack of diastereoselectivity in the reduction of the intermediate imine in the amination reaction (compounds 28 to 29). However diastereomers of this type are readily separable.

Figure 13C:
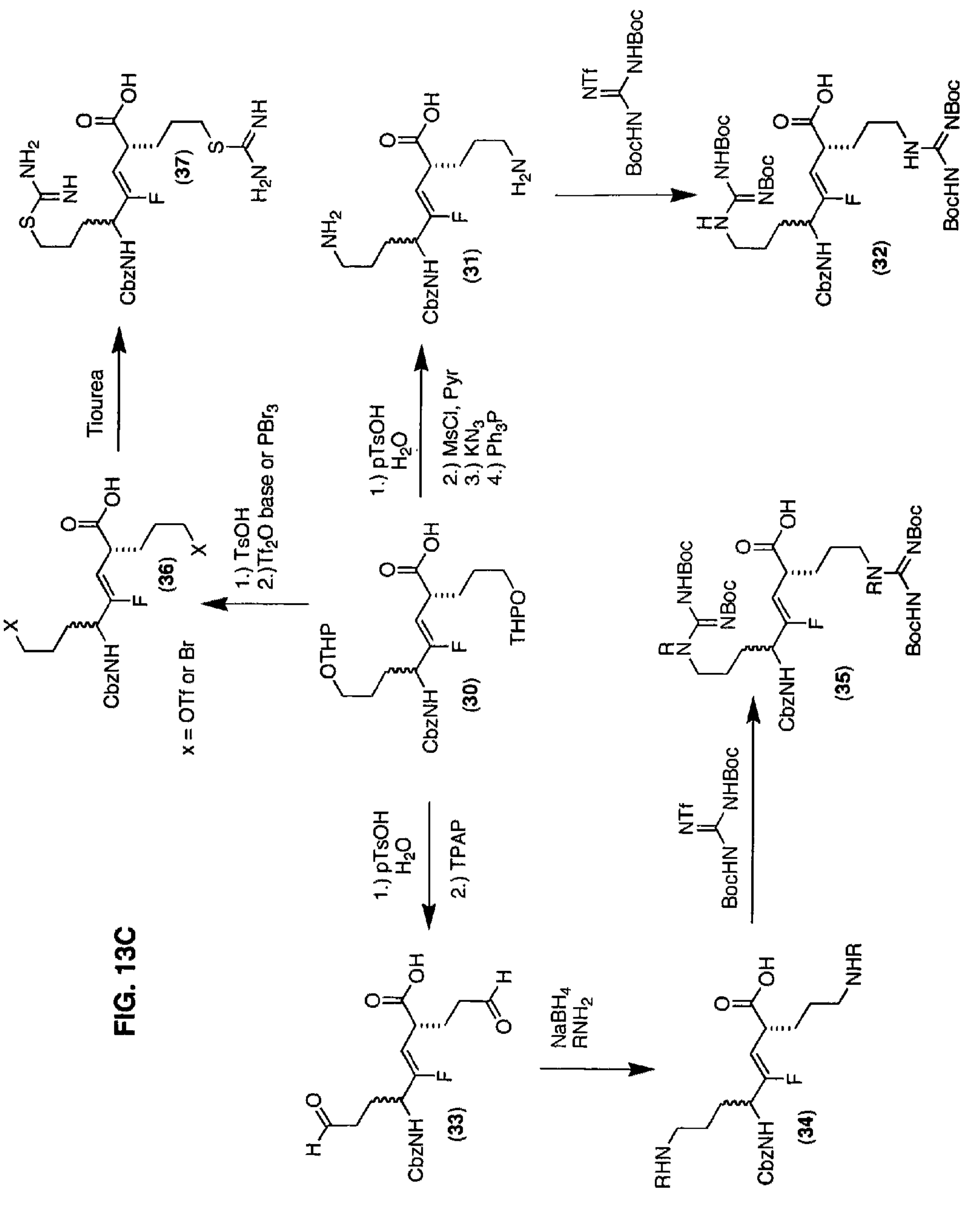

The bis-THP building block can be incorporated directly into peptides or be further modified with a number of different side chains prior to peptide synthesis. Two possible routes to the actual Arg-Arg mimic are presented in Scheme 3 (FIG. 13C). The THP group is removed and the alcohol converted to an amine (compound 31) by standard chemistry. Substitution of the mesylate with azide, followed by reduction, gives an amine that can be converted to a guanidine group (compound 32) by the method of Goodman (Feichtinger et al., 1998; Baker et al., 2000). The other route passes through an aldehyde (compound 33) which can be used to synthesize a variety of different substituted amines by reductive amination. This route allows for access to substituted guanidines. The intermediates on the path to the actual Arg-Arg mimics are also evaluated as inhibitors. The desired isothioureas are also availble from the THP ethers. Following deprotection, the alcohol is converted to a leaving group, either triflate or bromide (compound 36). Substitution with thiourea is the common approach to the desired isothioureas (compound 37) (King et al., 1982; Masquelin et al., 1998).

A number of different versions of the building block is then incorporated into different peptide sequences. The first structure to be tested is a direct analog of the Arg-Arg-Ile with the olefinic isostere replacing the Arg-Arg dimer (FIG. 13D, (compound 38)). If this molecule proves to be an inhibitor, a series of different structures will be examined where amino acids can be added to either end of the structure. The ability to add extra amino acids may be useful to modify inhibitor selectivity if that proves to be necessary. Given that a very small peptide sequence (trimer) has been found to be active it should be possible to develop a mimic that has reasonable stability and bioavailability to serve as a drug lead and demonstrate efficacy.

Example 11

Optimization of the High-throughput Hits for Activity, Selectivity and Bioavailability One set of compounds that appeared as hits are the biscyclohexyl acid and cyclohexylbenzoic acid compounds (compounds 1, 2 and 3). These hits appear to be very solid in that the three structures came out of three different libraries from two different commercial sources. That similar structures from independent sources appear as hits offers significant validation of those hits. Two other hits, also from different libraries and different commercial sources, are the thiophenes (compound 21) and (compound 22). Molecules of this type have been investigated for activity against TNF-a. While not proving to be particularly active, they did demonstrate oral availability (Fujita et al., 2002). There were a number of hits that contain either a guanidine or an isothioourea. This seems reasonable given that the small peptide identified herein is cleaved at an Arg-Arg site.

All of the hits in FIG. 12 are validated by "cherry picking" samples from the Harvard libraries. When these samples are received, in addition to assaying the compounds, their purity and identity is checked by LC-MS. All of these compounds are available from commercial sources and studied to determine their $IC_{50}$ and mode of action. While all the hits are tested to determine if they are valid. Initially, there are two that are examined to determine if their structures can be optimized by medicinal chemistry approaches.

Cyclohexylbenzene and Biscyclohexyl Hits

Compounds 1, 2 and 3 contains the structures of the cyclohexylbenzene and biscyclohexyl hits. Since there are 3 hits from 3 different libraries it is highly likely that this structure type is a valid hit. These three compounds have been ordered from suppliers other than the companies that provided the libraries. Once obtained, the molecules are checked for purity and identity and then assayed to validate their activity. Following validation, the $IC_{50}$ for the hits is determined. Additionally, these molecules are examined for their efficacy as completive inhibitors of Pla. The data from these hits serves as the baseline of medicinal chemistry studies that focuses on increasing activity and ultimately improving issues such as toxicity, in vivo stability and bioavailability.

The first derivatives tested are the biphenyl versions (compound 39) of the cyclohexylphenyl (compound 3) systems (FIG. 14A). If these structures have comparable activity they will provide greater ease of synthesis given that there are multiple reactions available for the coupling for two aryl rings. The biphenyl benzamide moiety has also been shown have activity as protease inhibitors, albeit serine protease (Quan et al., 1999). If biphenyls derivatives prove active, it will be a very simple matter to synthesize many derivatives from 4-borono-benzoic acid and the thousands of aryl bromides that are commerically available (Scheme 4; FIG. 14A).

Figure 14B:
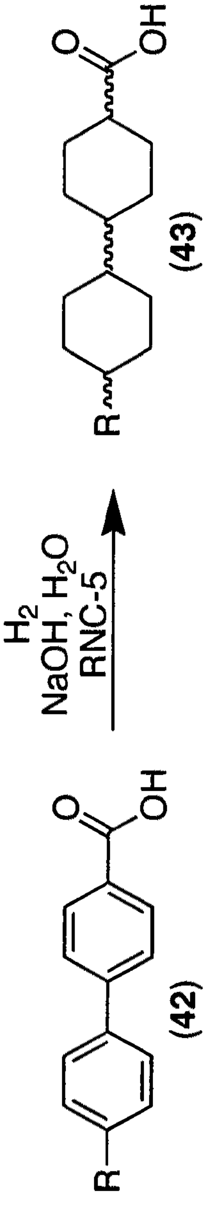
Figure 14C:
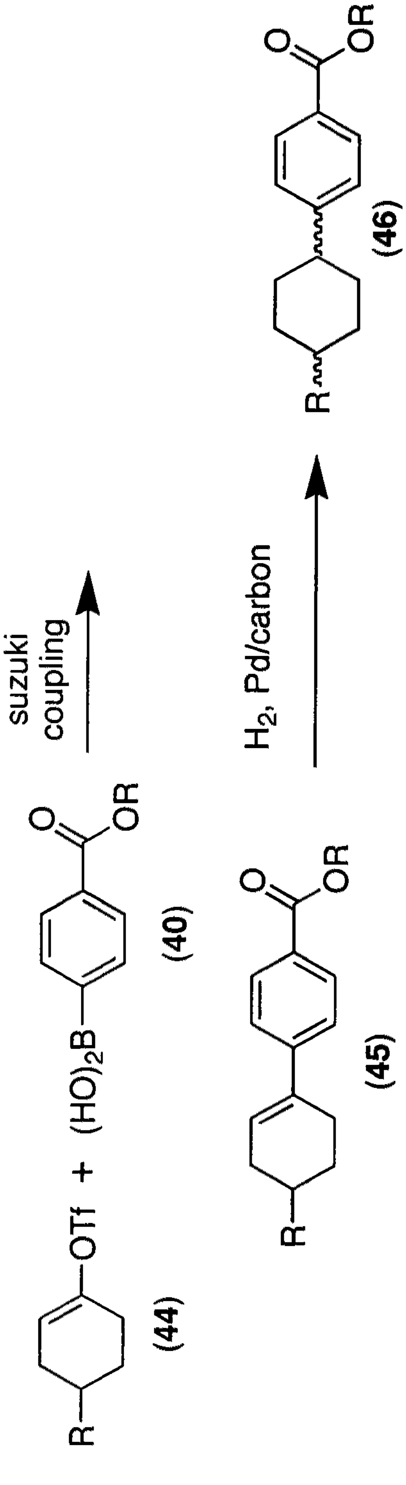

Additionally, this route is also used to provide access to some bicyclohexyl derivatives given that is possible to reduce the bi-aryl system to the saturated rings (Scheme 5; FIG. 14B). While this will not be general approach for all biaryls it should still provides a reasonable number of compounds for evaluation and comparison between the two scaffolds. If the cyclohexyl group proves to be essential for activity then individual derivatives of the active compounds will be synthesized by Suzuki reaction (Miyaura and Suzuki, 1995) of the 4-borono-benzoic acid with vinyl triflates followed by reduction of the double bond to give the saturated cyclohexane ring (Scheme 6; FIG. 14C). This approach has been chosen because the general nature of the reaction and the ready availability of vinyl triflates, which are synthesized from ketones, a diverse and plentiful source of structures. This provides access to a large number of different cyclohexane units since there are hundreds of commercially available cyclic ketones.

Figure 15A:
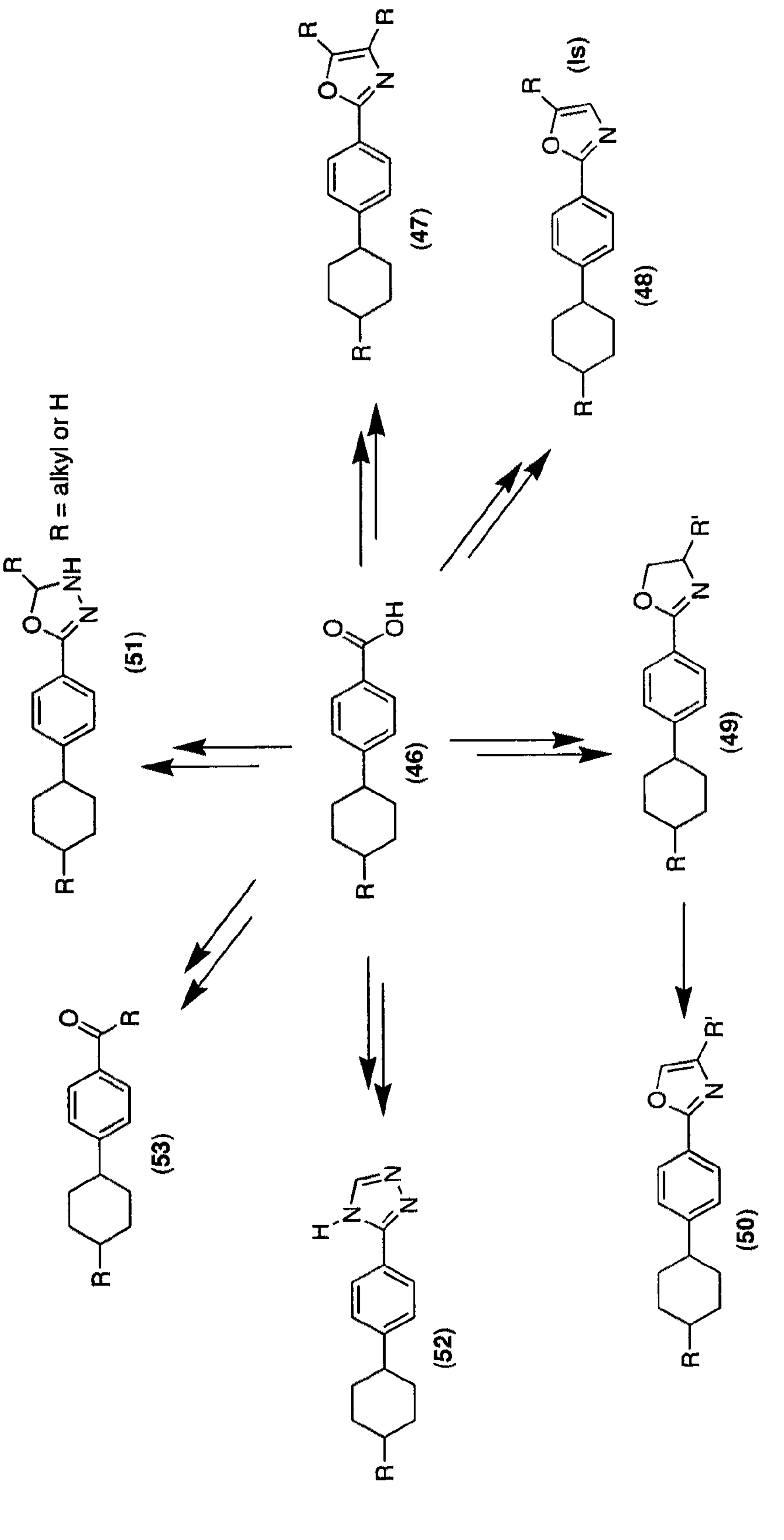
FIGS. 15A-15B show Thiophene hits.

Modifications at the other end of the molecule are also examined (Scheme 7; FIG. 15A). There are over 500 amines commercially available that could be used to synthesize unique amides. The acid group is also converted to a number of other potential pharmacophores including groups such as oxazoles (compounds 47, 48 50) (Dai et al., 2003; Yamane et al., 2004), oxazolines (compound 49) (Gilbertson and Lan, 2002; Agarkov et al., 2006), triazols (compound 52) (Kakefuda et al., 2002), oxadiazoline (compound 51) (Kakefuda et al., 2002) and ketones (compound 53).

Thiophene Hits

Figure 15B:
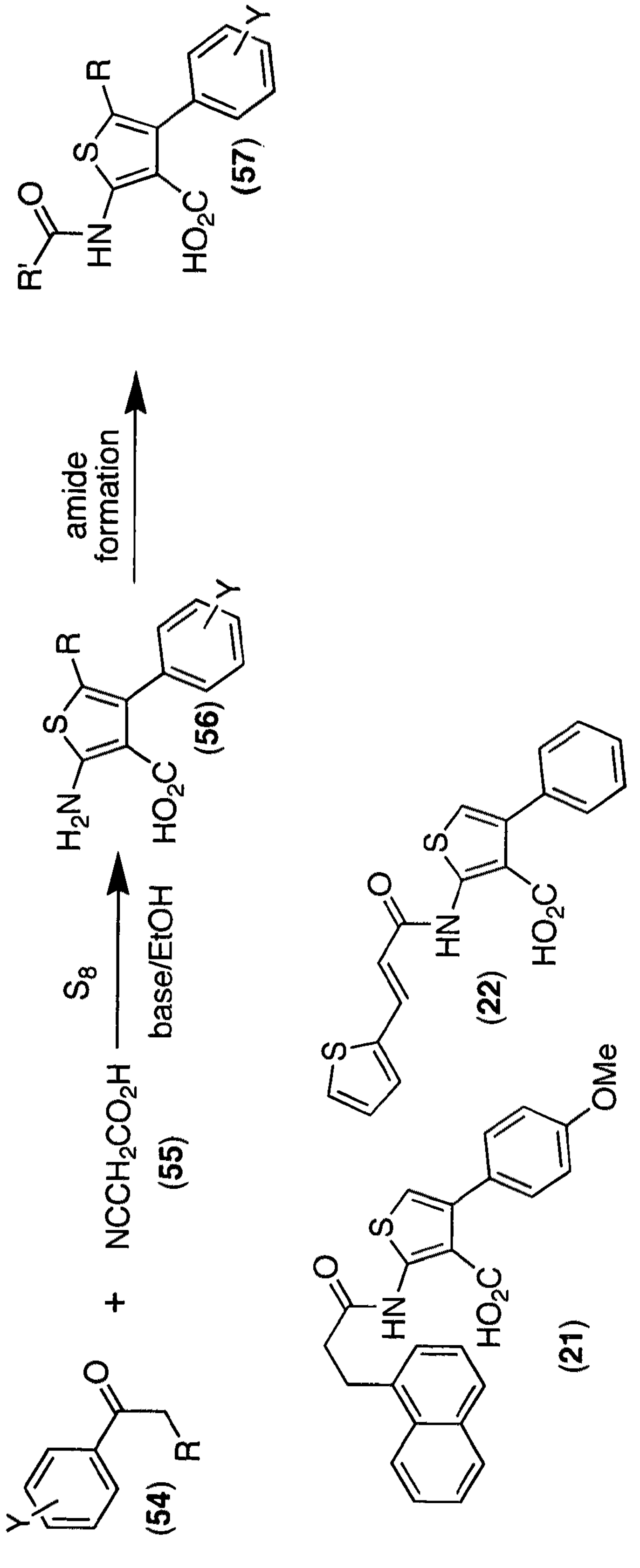

The other set of molecules that examined are the thiophene hits (Scheme 8; FIG. 15B). These hits are readily accessible by methods in the literature. The reaction of the ketone, methyl 2-cyanoacetate and elemental sulfur has been used to synthesize exactly these types of molecules. This approach provides access to structures with a variety of different aromatic rings attached. It has been shown to be a simple issue to make the necessary amides from the amino group (Fujita et al., 2002). Since versions of these structures have already been show to be orally available as TNF-a inhibitors, they appear to excellent examples to use in subsequent experiments if the necessary activity can be achieved.

Although two examples are discussed herein to point out the basic approach that will be taken, if one of the other hits appears to be more active based on its $IC_{50}$ then that structure type is pursued. By taking two different approaches, one based on turning small peptide substrates into inhibitors and the other using small molecule hits from a>50,000 compound screen, it is contemplated herein to identify a variety of inhibitors which can be used therapeutically and prophylactically.

The following references were cited herein:

Agarkov et al (2006) *Biopolymers* 84, 48-73.
Anderson G. et al. (1996) *Infect Immun* 64:4580-4585.
Baker et al (2000) *J Org Chem* 65, 9065-9058.
Barnet and Otake (1995) *J Org Chem* 60, 3107-3111.
Beesley E. et al. (1967) *J Bacteriol;* 94:19-26.
Benner G. E. et al. (1999) *Infect Immun;* 67:1922-1928.
Billich and Zocher (1990) *Biochem Pept Antibiot* 57-79.
Dai et al (2003) *Biorg Med Chem Lett* 13, 3817-3820.
Dive et al. (1992) *Intern'l Journal of Peptide & Protein Research* 39, 506-515.
Easterbrook T. et al. (1995) *Cont Microb Immunol;* 13: 214-215.
Feichtinger et al (1998) *J Org Chem* 63, 3804-3805.
Fischer (2003) *Current Protein and Peptide Science* 4, 339-356.
Fujita et al (2002) *Bioorg Med Chem* 10, 3113-3122.
Gilbertson and Lan (2002) *Tetrahedron Lett* 43, 6961-6965.
Goguen J. D. et al. (2000) *Methods;* 21:179-183.
Houghten, R. A. et al. (1991) *Nature* 354, 84-86
Kakefuda et al (2002) *Bioorg Med Chem* 10, 1905-1912.
King et al (1982) *J Am Chem Soc* 104, 7108-7122.
Kramer, R. A. et al. (2000) *Eur J Biochem;* 267, 885-893.
Kukkonen M. et al. (2001) *Mol Microbiol;* 40:1-16.
Kukkonen M. et al. (2004) *Mol Microbiol;* 51:215-225.
Kutyrev V. et al. (1999) *Infect Immunol;* 67:1359-1367.

Lähteenmäki K. et al. (1995) *FEMS Microbiol Rev;* 25:531-552.
Lähteenmäki K. et al. (1998) *Infect Immun;* 66:5755-5762.
Lähteenmäki K. et al. (2001) *FEBS Lett;* 504:69-72.
Lam K. S. et al. (1997) *Chem Rev;* 97:411-448.
Lathem, W. W. et al. (2007) *Science;* 315, 509-513.
Mason et al. (2003) *Current Opinion in Structural Biology* 13, 526-532.
Masquein et al (1998) *Helvet Chim Acta* 81, 646-660.
McDonough K. A. and Falkow S. (1989) *Mol Microbiol;* 3:767-775.
Miyaura and Suzuki (1995) *Chem Rev* 95, 2457-2483.
Perry, R. D. & Fetherston, J. D. (1997), *Clin. Microbiol. Rev;* 10, 35-66.
Quan et al (1999) *J Med Chem* 42, 2752-2759.
Rosse G. et al. (2000) *J Comb Chem;* 43: 305-341.
Sagan et al (2004) *Current Med Chem* 11, 2799-2822.
Sebbane, F. (2006) *Proc Natl Acad Sci USA* 103, 5526-5530.
Sodeinde O. A. and Goguen J. D. (1988) *Infect Immun;* 56:2743-2748.
Sodeinde O. A. et al. (1992) *Science;* 258:1004-1007.
Sodeinde O. A. and Goguen J. D. (1989) *Infect Immun;* 57:1517-1523.
Sodeinde O. A. et al. (1988) *Infect Immun;* 56:2749-2752.
Vandeputte-Rutten L. et al. (2001) *Embo J;* 20: 5033-5039.
Welkos S. L. and O'Brien A. (1994) *Methods Enzymol;* 235: 29-39.
Welkos, S. L. et al. (1997) *Microb Pathogen;* 23, 221-223
Yamane and Hea (2004) *Synthesis* 17, 2825-2832.
Zemla A. (2003) *Nucleic Acids Res;* 31:3370-3374.
Zhang et al. (1999) *J Biomol Screen* 4, 67-73.

---

What is claimed is:

1. A method of detecting omptin bacterial protease activity, comprising:

contacting a sample with an omptin bacterial protease substrate having an amino acid sequence of SEQ ID NOs: 5, 6, 7, 8, 9, 10, 11, 12, or 13, the substrate comprising (i) 3 to 6 amino acid residues, and (ii) an amino terminal quencher and a carboxy terminal fluorophore, or a carboxy terminal quencher and an amino terminal fluorophore; and measuring cleavage of the substrate by the protease to determine the presence or absence of the bacterial protease activity in the sample.

2. The method of claim 1, wherein said quencher is a 4-(4-dimethylaminophenylazo)benzoic acid, 3-nitro-4-hydroxy-L-phenyalanine or t-butoxycarbonyl.

3. The method of claim 1, wherein said bacterial proteases are a plasminogen activator of *Yersinia pestis*, an OmpT of *Escherchia coli*, a PgtE of *Salmonella* or a SopA of *Shigella flexneri*.

4. The method of claim 1, wherein said protease activity is detected by fluorometric assay, colorimetric assay or liquid chromatography mass spectrometry.

5. The method of claim 1, wherein the fluorophore is 5-((2-aminoethyl)amino)naphthalene-1-sulfonic acid, aminobenzoyl, or 7-methoxycoumarin-4yl)acetyl.

* * * * *

SEQUENCE LISTING

```
<160> NUMBER OF SEQ ID NOS: 15

<210> SEQ ID NO 1
<211> LENGTH: 14
<212> TYPE: PRT
<213> ORGANISM: Homo sapiens

<400> SEQUENCE: 1

Lys Lys Cys Pro Gly Arg Val Val Gly Gly Cys Val Ala His
1               5                   10


<210> SEQ ID NO 2
<211> LENGTH: 15
<212> TYPE: PRT
<213> ORGANISM: Bos primigenius

<400> SEQUENCE: 2

Lys Lys Cys Ser Gly Arg Ile Val Val Gly Gly Cys Val Ser Lys
1               5                   10                  15


<210> SEQ ID NO 3
<211> LENGTH: 24
<212> TYPE: PRT
<213> ORGANISM: Yersinia pestis

<400> SEQUENCE: 3

Lys Ser His Glu Met Leu Tyr Asp Ala Glu Thr Gly Arg Lys Ile Ser
1               5                   10                  15

Gln Leu Asp Trp Lys Ile Lys Asn
            20


<210> SEQ ID NO 4
<211> LENGTH: 31
<212> TYPE: PRT
<213> ORGANISM: Artificial Sequence
<220> FEATURE:
<223> OTHER INFORMATION: sythetic peptide

<400> SEQUENCE: 4

Lys Ser His Glu Met Leu Tyr Asp Ala Glu Thr Gly His His His His
1               5                   10                  15

His His Gly Arg Lys Ile Ser Gln Leu Asp Trp Lys Ile Lys Asn
            20                  25                  30


<210> SEQ ID NO 5
<211> LENGTH: 6
<212> TYPE: PRT
```

-continued

```
<213> ORGANISM: Artificial Sequence
<220> FEATURE:
<223> OTHER INFORMATION: Synthetic peptide with N terminal residue
      modified with DABCYL and the C terminal residue modified with
      EDANS and an amine group

<400> SEQUENCE: 5

Arg Arg Ile Asn Arg Glu
1               5


<210> SEQ ID NO 6
<211> LENGTH: 5
<212> TYPE: PRT
<213> ORGANISM: Artificial Sequence
<220> FEATURE:
<223> OTHER INFORMATION: synthetic peptide with N terminal residue
      modified with DABCYL and C terminal residue modified with hydroxyl
      group

<400> SEQUENCE: 6

Arg Arg Ile Asn Arg
1               5


<210> SEQ ID NO 7
<211> LENGTH: 4
<212> TYPE: PRT
<213> ORGANISM: Artificial Sequence
<220> FEATURE:
<223> OTHER INFORMATION: synthetic peptide with N terminal residue
      modified with DABCYL and C terminal residue modified with a
      hydroxyl group

<400> SEQUENCE: 7

Arg Arg Ile Asn
1


<210> SEQ ID NO 8
<211> LENGTH: 3
<212> TYPE: PRT
<213> ORGANISM: Artificial Sequence
<220> FEATURE:
<223> OTHER INFORMATION: synthetic peptide with N terminal residue
      modified with DABCYL and C terminal residue modified with a
      hydroxyl group

<400> SEQUENCE: 8

Arg Arg Ile
1


<210> SEQ ID NO 9
<211> LENGTH: 6
<212> TYPE: PRT
<213> ORGANISM: Artificial Sequence
<220> FEATURE:
<223> OTHER INFORMATION: synthetic peptide with N terminal residue
      modified with DABCYL and C terminal residue modified with EDANS

<400> SEQUENCE: 9

Arg Arg Ile Asn Arg Gln
1               5


<210> SEQ ID NO 10
<211> LENGTH: 6
<212> TYPE: PRT
<213> ORGANISM: Artificial Sequence
<220> FEATURE:
<223> OTHER INFORMATION: synthetic peptide with N terminal residue
      modified with DABCYL and C terminal residue modified with an amine
      group
```

<400> SEQUENCE: 10

Arg Arg Ile Asn Arg Gln
1 5

<210> SEQ ID NO 11
<211> LENGTH: 6
<212> TYPE: PRT
<213> ORGANISM: Artificial Sequence
<220> FEATURE:
<223> OTHER INFORMATION: synthetic peptide with N terminal residue modified with pABA and C terminal residue modified with EDANS

<400> SEQUENCE: 11

Arg Arg Ile Asn Arg Gln
1 5

<210> SEQ ID NO 12
<211> LENGTH: 4
<212> TYPE: PRT
<213> ORGANISM: Artificial Sequence
<220> FEATURE:
<223> OTHER INFORMATION: synthetic peptide with N terminal residue modified with DABCYL and C terminal residue modified with EDANS and an amine group

<400> SEQUENCE: 12

Arg Arg Ile Asn
1

<210> SEQ ID NO 13
<211> LENGTH: 3
<212> TYPE: PRT
<213> ORGANISM: Artificial Sequence
<220> FEATURE:
<223> OTHER INFORMATION: synthetic peptide with N terminal residue modified with DABCYL and C terminal residue modified with EDANS and an amine group

<400> SEQUENCE: 13

Arg Arg Ile
1

<210> SEQ ID NO 14
<211> LENGTH: 28
<212> TYPE: PRT
<213> ORGANISM: Artificial Sequence
<220> FEATURE:
<223> OTHER INFORMATION: synthetic peptide

<400> SEQUENCE: 14

Lys Gly Gly Thr Gln Thr Ile Asp Lys Asn Ser Gly Asp Ser Val Ser
1 5 10 15

Ile Gly Gly Asp Ala Ala Gly Ile Ser Asn Leu Asn
20 25

<210> SEQ ID NO 15
<211> LENGTH: 3
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: modified with DABCYL
<220> FEATURE:
<221> NAME/KEY: MOD_RES -continued

```
<222> LOCATION: (3)..(3)
<223> OTHER INFORMATION: Xaa is Ala, Ile, Val, Thr, Ser, Cys, or Gly and
      modified with EDANS and an amine group

<400> SEQUENCE: 15

Arg Arg Xaa
1
```